United States Patent [19]
Neill et al.

[11] Patent Number: 5,728,374
[45] Date of Patent: *Mar. 17, 1998

[54] HAIR MANAGEABILITY AND STYLING COMPOSITION AND METHOD

[75] Inventors: Paul Neill, Hinsdale; Loralei Brandt, Cary; Priscilla Walling, Darien; Arun Nandagiri, Libertyville; Norman Meltzer, Morton Grove, all of Ill.

[73] Assignee: Helene Curtis, Inc., Chicago, Ill.

[*] Notice: The term of this patent shall not extend beyond the expiration date of Pat. No. 5,589,163.

[21] Appl. No.: 634,180

[22] Filed: Apr. 18, 1996

Related U.S. Application Data

[63] Continuation of Ser. No. 355,653, Dec. 14, 1994, Pat. No. 5,589,163, which is a continuation-in-part of Ser. No. 194,067, Feb. 9, 1994, Pat. No. 5,447,806.

[51] Int. Cl.$^6$ .................... A61K 7/09; A61K 7/06
[52] U.S. Cl. .................... 424/70.51; 424/70.5; 424/70.2; 132/204
[58] Field of Search .................... 424/70.2, 70.4, 424/70.5, 70.51; 132/204

[56] References Cited

U.S. PATENT DOCUMENTS

| | | | |
|---|---|---|---|
| 5,208,014 | 5/1993 | Dubief | 424/70.51 |
| 5,332,570 | 7/1994 | Bengstrom | 424/70.51 |

FOREIGN PATENT DOCUMENTS 5762217  10/1977  Japan.

*Primary Examiner*—Sally Gardner-Lane
*Attorney, Agent, or Firm*—Marshall, O'Toole, Gerstein, Murray & Borun

[57] ABSTRACT

A mild permanent wave reducing agent-containing composition and method of permanently waving or straightening human hair that provides a strong, long lasting curl, or long lasting straight hair formation, while minimizing hair damage. The composition includes two ionic compounds, one cationic and the other anionic, that complex in solution over a molar ratio of cationic compound to anionic compound in the range of about 1:1.2 to about 1.2:1, preferably in the range of about 1:1.1 to about 1.1:1, to provide synergy in waving efficiency, thereby providing a strongly reconfigured hair configuration (curled or straightened). At least one of the ionic compounds functions as a reducing agent for hair, capable of breaking the disulfide bonds in the hair so that the bonds later can be reformed via oxidation, when the hair is in the desired configuration. Examples of cationic compounds include thiocholine, choline, cysteineamide, cysteamine, and combinations thereof. Examples of anionic compounds include cysteine, N-acetylcysteine, thioglycolic acid or its salts, and combinations thereof. The preferred ionic compounds are thiocholine and N-acetylcysteine. The composition is effective over a wide pH range of about 4 to about 12, especially about 5.0 to about 9.4, preferably in the range of about 5.5 to about 8.5, and more preferably at a neutral pH of about 7.0 ±1.0.

32 Claims, 18 Drawing Sheets

HAIR MANAGEABILITY AND STYLING COMPOSITION AND METHOD

CROSS-REFERENCE TO RELATED APPLICATIONS

This application is a continuation of U.S. patent application Ser. No. 08/355,653, filed Dec. 14, 1994, now U.S. Pat. No. 5,589,163 which is a continuation-in-part of U.S. patent application Ser. No. 08/194,067, filed Feb. 9, 1994, now U.S. Pat. No. 5,447,806.

FIELD OF THE INVENTION

The present invention is directed to a hair reducing agent-containing permanent wave lotion and method for reshaping, curling, curl relaxation of, straightening and/or bodifying human hair, particularly useful for forming a lasting curl pattern. More particularly, the present invention is directed to a composition and method capable of permanently reshaping human hair without significant additional damage.

BACKGROUND OF THE INVENTION AND PRIOR ART

In general, permanent waving of human hair is achieved by chemically breaking the sulfur to sulfur or disulfide cystine bonds occurring naturally in human hair and then reforming the Cystine bonds while the hair is wrapped or curled on rods. The sulfur to sulfur cystine bonds in human hair maintain the hair in a naturally straight or curly configuration and, in order to permanently reshape the hair into a lasting, different configuration, a significant percentage of the sulfur to sulfur bonds must be broken and then reestablished after the hair is reconfigured in a desired position, such as wrapped around a suitable mandrel or roller. In general, the sulfur to sulfur cystine bonds are broken with a waving lotion composition, containing a reducing agent, and after the hair is wound into a curl formation around a rod or roller, the sulfur to sulfur cystine bonds are relinked or reestablished while the hair is in the curl formation by contacting the hair, in the new formation, with an oxidizing agent, such as hydrogen peroxide or a water-soluble bromate.

As set forth in U.S. Pat. No. 5,116,608 others have used a reducing agent composition that is a quaternary ammoniomercaptan, such as thiochloline, or its salts, and discloses that the addition of a second reducing agent, such as thioglycolic acid, cysteamine or cysteine, is not detrimental to the reducing action of the ammoniomercaptan. Also an N-acylcysteamine $HSCH_2CH_2NH—COR(R=2-10$ C alkyl), as a hair reducing compound, has been used together with another reducing agent selected from the group consisting of cysteine, acidic sodium hyposulfite, sodium sulfite, thioglycerol and thiolactic acid, as disclosed in Japanese Patent HEI 2-53714. Miyazaki, et al. U.S. Pat. No. 4,139,610 discloses a combination of cysteine and N-acetylcysteine. This Assignee's Nandagiri, et al. U.S. Pat. No. 5,260,054 discloses cysteamine as a reducing agent, and Showa Japanese Patent 57062217 (Application No. 55-136857) discloses cysteamine together with an optional second reducing agent. U.S. Pat. No. 5,165,427 discloses cysteinamide as a reducing agent. U.S. Pat. No. 5,223,252 discloses a combination of a thioglycolate and cysteine at a pH of 7.5 to 9.5. U.S. Pat. No. 5,332,570 discloses a combination of cysteamine hydrochloride and a thio compound, such as monoethanolamine thioglycolate (MEATG), at a weight ratio of about 40:60, together with isoascorbic acid.

The reducing action of mercaptans on keratin is due mostly to the dissociated form of the thiol groups, the thiolate anion. "Acid" permanent waves sufficiently curl hair at a lower pH compared to alkaline permanent waves, e.g., at about 8.0 and above, because the waving agents in these permanent waves have low pKa values and thus exist predominantly in dissociated (thiolate) format a pH approaching neutral. Hence, the Pka value shows that some mercaptans are efficient at high pH while others with a low Pka value and high ionization constant are efficient at lower pH values. Therefore, it is generally understood, by those skilled in the art, that acceptable waving efficiency is usually obtained by working near the Pka of the active reducing agent. For example, it is well known that the alkaline salts of thioglycolic acid, e.g., the ammonium salt of thioglycolic acid (Pka=10.4) has acceptable waving efficiency only if the pH of solution exceeds 9, see Zviak, Charles, The Science of Hair Care, Permanent Waving and Hair Straightening, p. 191, 1986; while amides such as thioglycolamide (Pka=8.4), and esters such as glycerol thioglycolate (Pka=7.8) give acceptable waving efficiency at neutral and even slightly acid Ph.

Different reducing agents are effective to break the cystine bonds that cross link human hair protein at the different pHs. Generally speaking, the acid permanent wave compositions having a lower pH include reducing agents such as bisulfites, e.g., ammonium bisulfite, or glycerol monothioglycolate, capable of breaking the sulfur to sulfur cystine bonds within lower pH ranges, whereas the alkaline permanent wave compositions, having pHs in the range of about 7.5 to 9.5, require an alkaline salt of thioglycolic acid so that the alkali can penetrate and swell the hair shaft for easier penetration of the reducing agent in order to break the sulfur to sulfur cystine bonds.

The use of diammonium dithiodiglycolate in acid or alkaline permanent wave lotions allows greater flexibility in processing time because it minimizes the possibility of overprocessing. This is due to the fact that the reaction of thioglycolic acid (TGA) with hair keratin is an equilibrium process. Thus by including diammonium dithiodiglycolate (oxidized TGA) in the wave lotion, the rate of the reaction of the thioglycolic acid with hair keratin is decreased and prevented from going to completion.

It is theorized that somewhere in the range of about 20% to about 60% of the natural sulfur to sulfur cystine bonds in the hair shafts should be broken in order to give the hair the capability of being reshaped to any desired shape, such as curled around a rod or roller, or straightened, and capable of retaining this new shape. If too few of the sulfur to sulfur bonds are broken, the natural or normal configuration of the hair will predominate, causing the hair to retain its previous shape. This is because the predominant prior or natural bonds in the hair dictate that the hair will remain in the old configuration or shape. Hydrogen bonds are physically broken when wet hair is stretched and wrapped around a roller. When the hair is dried, the hydrogen bonds are reformed in a curled position or shape. While the hydrogen bonds aid to maintain the hair in the new configuration, the sulfur to sulfur cystine bonds are much stronger and, to a much greater extent than the hydrogen bonds, control the efficacy of the permanent wave.

In order to successfully provide a satisfactory permanent wave in the hair, the sulfur to sulfur cystine bonds reformed in the hair in the new or curled configuration, when the hair is later oxidized with the neutralizing agent, should be stronger than the prior or natural cystine hair bonds. It is desired, therefore, when permanent waving, that enough new bonds in a new hair configuration are formed during permanent waving to outnumber the old bonds remaining that tend to form the hair in its prior or natural configuration, whether it be straight or naturally curled.

Since damaged hair already has a significant number of the sulfur to sulfur cystine bonds broken due to some chemical, mechanical or environmental abuse, particularly the chemical abuses, such as bleaching, tinting or frosting, it is difficult to determine what length of time, and what reducing agent concentration to apply to the hair to provide the hair with the proper number of sulfur to sulfur bonds remaining after the reducing agent treatment. Significantly damaged hair, such as bleached hair, may require a reducing agent lotion application for a period of only about 5 minutes whereas normal hair, not significantly damaged, may require the reducing agent lotion for a period of approximately 20 minutes under the same reducing agent concentration and temperature in order to result in both the damaged and normal hair having approximately the same curl configuration. Ideally, after the reducing agent treatment, every one of the hair shafts treated will contain the same ratio of broken to unbroken bonds so that this same ratio can be reestablished in each hair shaft when the hair is in the new configuration to provide a consistent strong curl over the entire head of hair.

Generally, the reducing agent lotion is applied to the hair by first shampooing the hair and then applying the reducing agent lotion to the hair, either before or after the hair is wrapped around suitable rollers. Since it is not possible for even the experienced permanent wave applier to accurately determine visually the extent of damage to the hair in order to have a better idea of how long the reducing agent should be in contact with the hair, it is necessary to take a "test curl" so that after a predetermined amount of time, for example 10 minutes, a first roller is removed from the hair and the curl is felt and stretched in an attempt to determine if the curl formation is strong enough. Once it is determined that the reducing agent has been in contact with the hair for a sufficient time period, the hair is rinsed thoroughly with water while still on the rollers or rods and, while the hair remains on the rollers or rods, a neutralizing agent is applied to oxidize and reform the sulfur to sulfur bonds while the hair is in the new, rolled configuration- The neutralizing agent contains an oxidizing agent, such as hydrogen peroxide or a bromate salt, in order to reestablish the sulfur to sulfur bonds to leave the hair in a relatively permanent, e.g., 2–4 months, new configuration. The rods are removed, before or after rinsing out the neutralizing agent.

When the reducing agent lotion is applied to sections of the head prior to rolling that portion of the hair onto the rods it is called a lotion wrap whereas when the hair is rolled on the rods or rollers first and then the lotion applied onto all of the hair after rolling, this is called a water wrap. The timing for the reducing agent to be in contact with the hair for a lotion wrap is begun from the time that all rods are on the head, and the timing for a water wrap begins from the time that the lotion application is completed. The capability of using a water wrap is clearly more desirable since the lotion is applied to the entire head of hair all at once in a short period of time and can be rinsed from the hair all at once to provide a more uniform reducing agent contact time for all of the hair.

Other prior art patents directed to permanent waving compositions intended to permanently wave both normal and damaged hair are found in the Klemm et al. U..S. Pat. No. 4,273,143; and Cannel et al. U.S. Pat. No. 4,301,820. Japanese Patent No. 57-212110 appears to be directed to a post-permanent treatment containing glycerine to give hair sheen and luster.

SUMMARY OF THE INVENTION

In brief, the present invention is directed to a mild permanent wave reducing agent-containing composition and method of permanently waving or straightening human hair that provides a strong, long lasting curl, or long lasting straight hair formation, while minimizing hair damage. The composition generally includes two different ionic compounds, one cationic and the other anionic, that are believed to complex in solution at molar ratios of about 1:1.2 to about 1.2:1, preferably about 1:1.1 to about 1.1:1, to provide synergy in waving efficiency, thereby providing a strongly reconfigured hair configuration (curled or straightened). At least one of the ionic compounds functions as a reducing agent for hair, capable of breaking the disulfide bonds in the hair so that the bonds later can be reformed via oxidation, when the hair is in the desired configuration. Examples of cationic compounds include thiocholine, choline, cysteine, cysteamine, monoalkyl, dialkyl and trialkyl cysteamines, such as dimethyl cysteamine, or one of their salts, e.g., hydrochloride, cysteineamide, and combinations thereof. Examples of anionic compounds include thioglycolic acid and its salts, particularly ammonium thioglycolate or monoethanolamine thioglycolate (MEATG); cysteine and its salts; N-acetylcysteine and its salts; and combinations thereof. While cysteine is included in both the cationic category and in the anionic category, both compounds cannot be cysteine while achieving effective complexing. Cysteine can have both cationic and anionic characteristics depending on pH of the solution and other factors. The preferred ionic compounds are thiocholine and N-acetylcysteine or cysteamine and a thioglycolic acid or thioglycolic acid salt, particularly monoethanolamine thioglycolate (MEATG). The composition is effective over a wide pH range of about 2 to about 12, especially about 5.0 to about 9.4, preferably in the range of about 5.5 to about 8.5, and more preferably at a neutral pH of about 7.0±1.0.

Quite surprisingly, combinations of thioglycolic acid or its salts, e.g., ammonium thioglycolate or monoethanolanine thioglycolate (MEATG), as the anion, together with a cation, for example, cysteamine or thiocholine, complex within a molar ratio of cationic compound to anionic compound in the range of about 1:1.2 to about 1.2:1, preferably about 1:1.1 to about 1.1:1, to provide synergistic waving efficiencies at a pH in the range of about 2.0 to about 12, particularly in the range of about 2.0 to about 8.5, especially about 5.5 to about 8.0. This is contrary to the teachings of the prior art which discloses that thioglycolic acid or its salts are only effective at a pH of about 9.0 or above.

Each ionic compound is included in the composition in a concentration of about 0.2M (molar) to about 4M, or up to the limit of the solubility of each compound. Particularly surprising wave efficiencies are found at concentrations of about 0.5M to about 1.5M, preferably about 0.6M to about 1.0M, for each ionic compound, with best results at a concentration of 0.73M for each ionic compound.

The waving lotion of the present invention is easy to use and apply without damaging the hair while providing a strong, tight curl and leaving the hair soft. The composition can be lotion or water wrapped and can be used with or without heat. Unexpectedly, the composition is applied to any type of hair, regardless of structural damage to the hair, resulting in consistent curl tightness and softness and the composition can be applied much more frequently than most prior art permanent wave compositions without significant damage to the hair. Further, the permanently waved hair can be washed repeatedly without significant loss of curl tightness.

Accordingly, one aspect of the present invention is to provide a new and improved permanent wave composition capable of breaking sulfur to sulfur bonds in human hair so that the hair can be reconfigured in a different configuration. The sulfur to sulfur human hair bonds can be reestablished with an oxidizing agent to maintain the new hair configuration for a substantial time period.

Another aspect of the present invention is to provide a new and improved permanent wave lotion containing a combination of cationic and anionic compounds that are believed to form an ionic complex, in solution, within a molar ratio of cationic compound to anionic compound in the range of about 1:1.2 to about 1.2:1, preferably about 1:1.1 to about 1.1:1, that functions as a reducing agent capable of breaking sulfur to sulfur hair bonds without causing further significant damage to tinted, frosted, bleached or other substantially damaged hair. The formation of the ionic complex was confirmed by both nuclear magnetic resonance (NMR) and infrared (IR) analysis comparing cationic and anionic compounds alone to the combination, in solution.

Another aspect is to provide a waving lotion containing both cationic and anionic components that combine to provide surprisingly better waving efficiency than either component alone. Still another aspect of the present invention is to provide a new and improved permanent wave lotion that has excellent wave efficiency at a near neutral pH.

These and other objects and advantages of the present invention will become apparent from the following detailed description of the preferred embodiments.

DETAILED DESCRIPTION OF THE PREFERRED EMBODIMENTS

The present invention is directed to a permanent wave composition containing a cationic compound and an anionic compound that complex in solution at a molar ratio of cationic compound to anionic compound in the range of about 1:1.2 to about 1.2:1, preferably about 1:1.1 to about 1.1:1, to provide synergy in wave efficiency, thereby providing a strongly held, new hair configuration. At least one of the ionic compounds functions as a reducing agent for hair and is capable of breaking the disulfide bonds in the hair so that the hair can be set in a different configuration—either curled or straightened.

The cationic portion of the reducing agent of the present invention should be a compound within one of the following two structural formulae:

wherein $R_1$, $R_2$, $R_3$, $R_5$, $R_6$ and $R7$, same or different, are H, an alkyl group or hydroxyalkyl group having 1 to 4 carbons, preferably 1 to 3 carbon atoms; and $R_4$ is OH, —$OR_8$ or —$NR_9R_{10}$, wherein $R_8$, $R_9$ and $R_{10}$, same or different, are H, an alkyl group or hydroxyalkyl group having 1 to 4, preferably 1 to 3, carbon atoms.

A is an alkylene group having 1 to 5, preferably 1 to 3, carbon atoms;

B is O or S; and

X, Z (same or different) is OH, a halogen atom, $NO_3$, $SO_2$ or $R_{11}OSO_3$, wherein $R_{11}$ is an alkyl group having 1 to 5, preferably 1 to 3, carbon atoms.

Preferred examples of specific compounds falling within structural formula I are choline, thiocholine, cysteamine, monoalkyl, dialkyl and trialkyl cysteamines. A preferred example of a compound falling within structural formula II is the methyl ester of cysteine.

In accordance with an important feature of the present invention, the cationic compound(s) of formulae I or II complex in solution with a compound that forms a thiocarboxylate anion (formula III):

 (III)

in solution, where A is nonexistent, or is an alkylene group having 1 to 4, preferably 1 to 3, carbon atoms, and Y is H, OH, $NH_2$ or

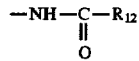

wherein $R_{12}$ is an alkyl group having 1 to 4, preferably 1 to 3, carbon atoms. Specific examples of compounds that form the thiocarboxylate anion (III) are monoethanolamine thioglycolate (MEATG), thioglycolic acid, cysteine, and N-acetylcysteine. The preferred ion pairs are thiocholine and N-acetylcysteine; or cysteamine and monoethanolamine thioglycolate (MEATG).

Figure 1:
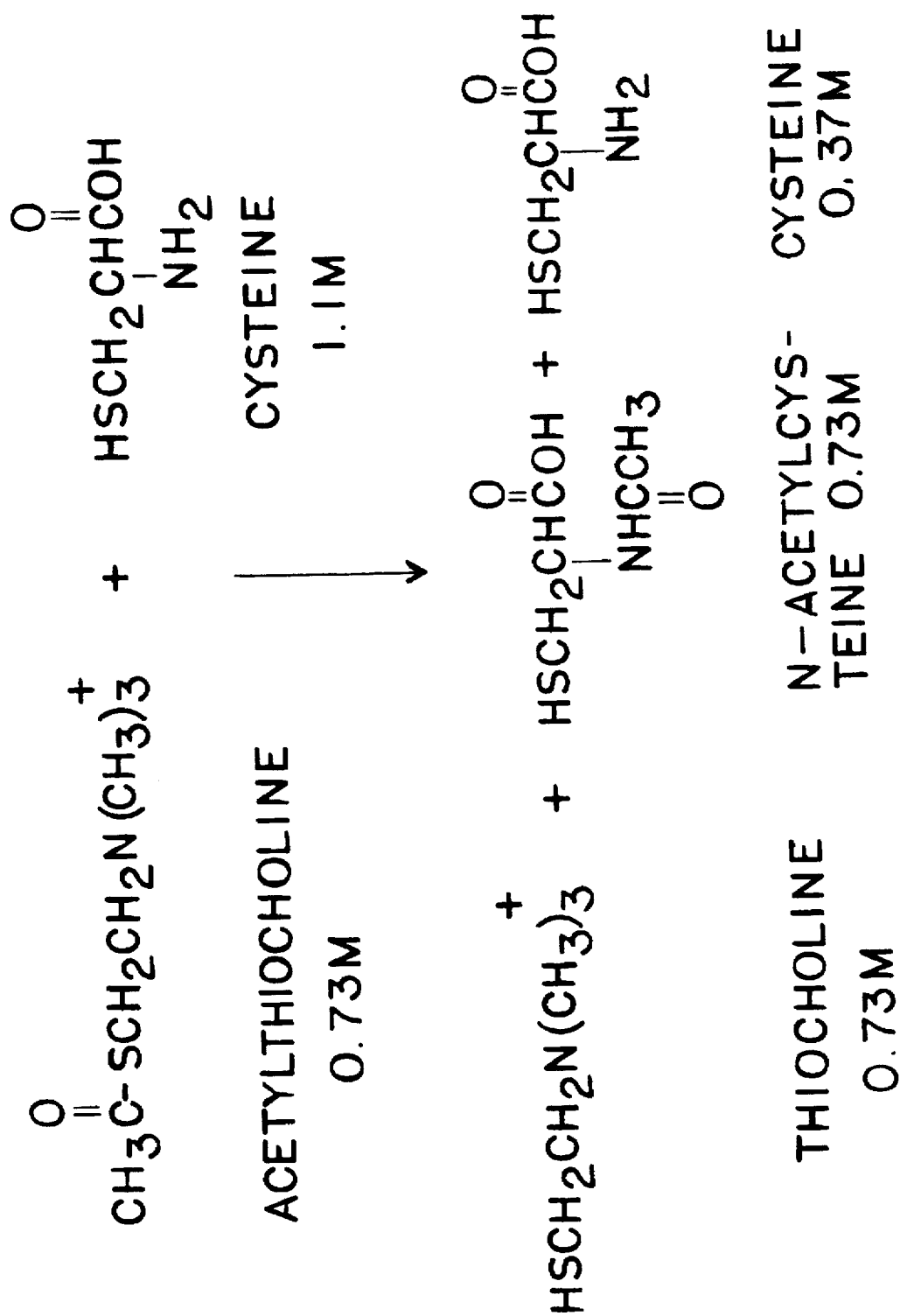
FIG. 1 is a chemical equation for one embodiment of the present invention showing a reaction between acetylthiocholine and cysteine (in molar excess) to yield a synergistic combination of thiocholine and acetylcysteine, and excess cysteine.

In one embodiment, the cationic compound is thiocholine and the anionic compound is N-acetylcysteine (see FIG. 1). The composition is effective over a wide range of pH of about 2.0 to about 12.0, particularly in the range of about 5.0 to about 9.4, preferably in the range of about 5.5 to about 8.5 and more preferably at a near neutral pH of about 7.0±1.0. Both thiocholine and N-acetylcysteine are available commercially and can be mixed separately in amounts up to their limits of solubility. If added in equal molar concentrations, the limit for their solubilities in a water carrier is up to about 3.0M thiocholine and 3.0M N-acetylcysteine. If one of the compounds is added in a lesser amount, the amount of the other compound that can be solubilized in a water carrier goes up proportionately.

Although thiocholine is available commercially, it is presently very costly and would not be economical to include in a commercial permanent waving lotion at its present cost. Accordingly, it has been found that thiocholine and N-acetylcysteine can be formed by the in-situ reaction of an acetylthiocholine and cysteine (preferably in excess) to produce thiocholine, N-acetylcysteine, and preferably an excess of cysteine, as shown in FIG. 1. When formed by the reaction of acetylthiocholine and cysteine, it is preferred that the cysteine reactant is provided in molar excess of the quantity of the acetylthiocholine since acetylthiocholine is toxic in high concentrations. An excess of cysteine ensures that there is essentially no unreacted acetylthiocholine remaining in the waving lotion composition.

As will be made more apparent hereinafter, it has been found that the optimum concentration for acetylthiocholine is about 0.73M. When reacting acetylthiocholine with cysteine to provide thiocholine and N-acetylcysteine in-situ, therefore, it has been found that the optimum concentration for each reactant is 0.73M acetylthiocholine and about 0.9M to about 1.5M cysteine, preferably about 1.1M cysteine, to ensure that all of the acetylthiocholine is reacted with the cysteine to provide thiocholine at a concentration of about 0.73M, an equal concentration of N-acetylcysteine at 0.73M and an excess of cysteine at a concentration of about 0.17M to about 0.77M, preferably about 0.37M, as shown in FIG. 1. It should be understood that the excess cysteine does not aid in or reduce the wave efficiency of the composition, particularly at a neutral pH of about 7.0. As is understood in the art, cysteine is effective as a reducing agent in a waving lotion only at a pH of about 9.0 and above.

Figure 2:
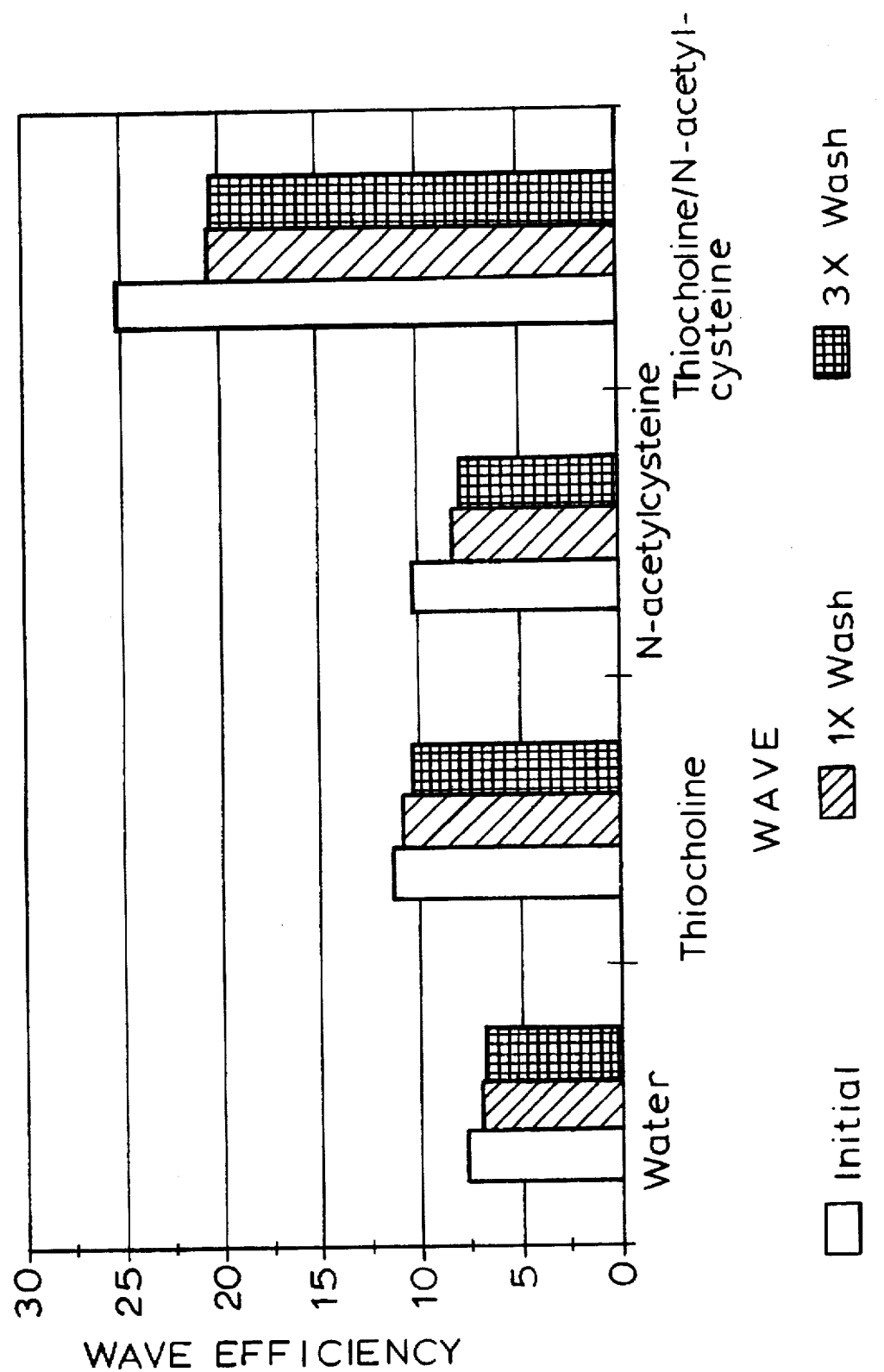
FIG. 2 is a bar graph showing the wave efficiency of thiocholine and N-acetylcysteine, each separately, compared to the synergistic wave efficiency effects of the combination, prior to washing, and after one and three washes, compared to a water control.

The surprising and synergistic wave efficiencies obtained with a combination of thiocholine and N-acetylcysteine are shown in FIG. 2. In obtaining the data shown in FIG. 2, hair tresses were treated with a waving lotion containing only water as a control; 0.73M thiocholine; 0.73M N-acetylcysteine; and the combination of 0.73M thiocholine and 0.73M N-acetylcysteine. The waving efficiency data shown in Table I were used to form FIG. 2.

As shown in Table I and FIG. 2, neither thiocholine nor N-acetylcysteine was much more effective than water, by itself, in curl formation. Surprisingly, the combination of thiocholine and N-acetylcysteine provided more than twice the wave efficiency of either thiocholine or N-acetylcysteine used alone. Further, as shown in Table I and FIG. 2, the wave efficiency for the combination of thiocholine and N-acetylcysteine after one and three washings remained about 80% of its maximum prior to washing.

TABLE I

SYNERGISTIC EFFECT

| Wave | Waving Efficiency | | |
|---|---|---|---|
| | Initial | 1× Wash | 3× Wash |
| Water | 7.8 | 7.13 | 6.8 |
| Thiocholine | 11.4 | 10.96 | 10.42 |
| N-acetylcysteine | 10.3 | 8.33 | 8 |
| Thiocholine/N-acetylcysteine | 25.2 | 20.61 | 20.39 |

Figure 3:
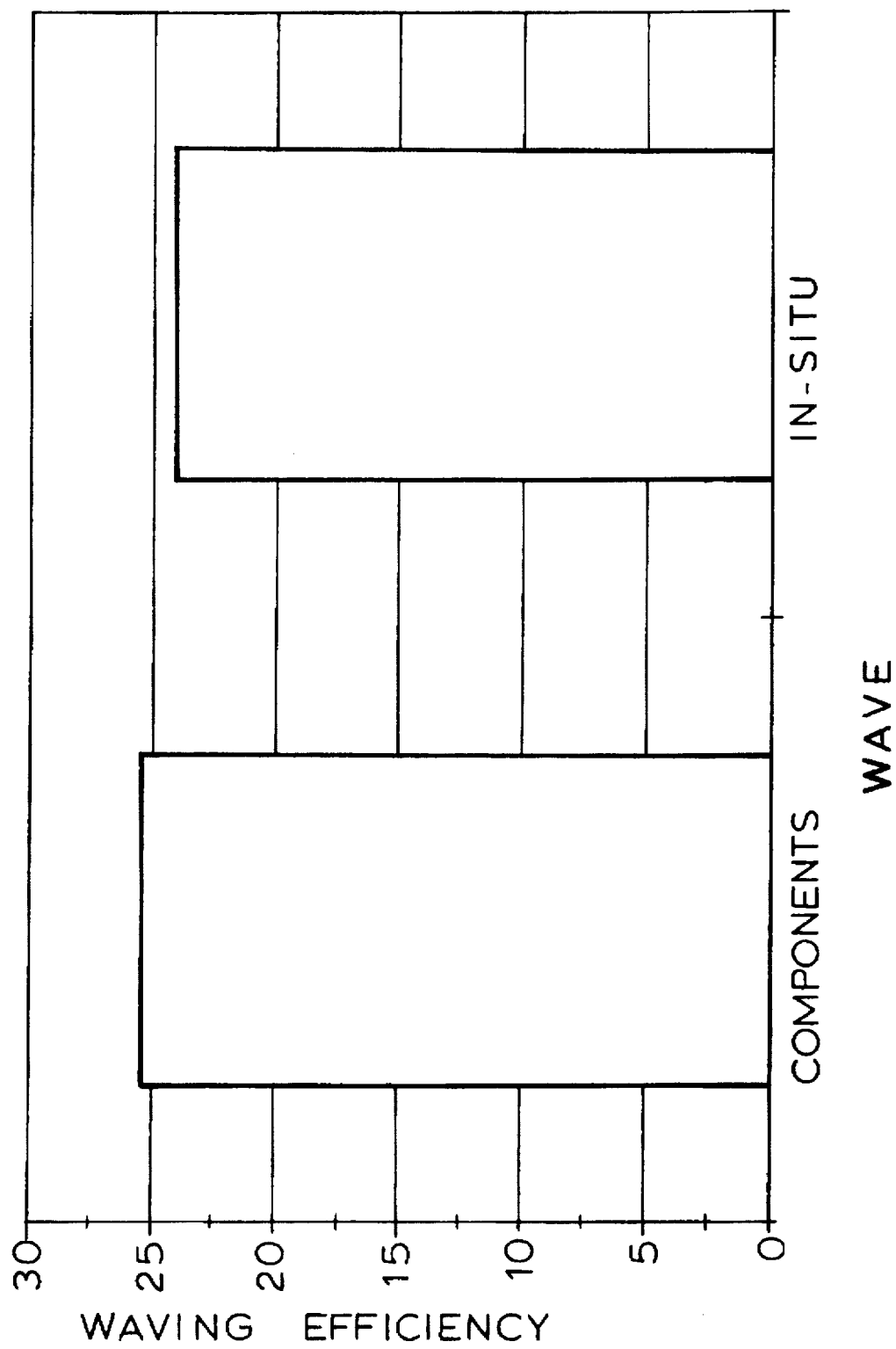
FIG. 3 is bar graph comparing the wave efficiency of a permanent wave lotion prepared by mixing thiocholine and acetylcysteine (ionic components) compared to the wave efficiency of the permanent wave lotion prepared by mixing acetylthiocholine with cysteine, which react to provide thiocholine and acetylcysteine reaction products, in-situ, at 0.73M for each ionic component.

Waving lotions were prepared by adding separate components—thiocholine and N-acetylcysteine— each at a concentration of 0.73M, in comparison to another waving lotion prepared by the in-situ reaction of acetylthiocholine and cysteine in the molar amounts shown in FIG. 1. The following data set forth in Table II and in FIG. 3 show that the wave efficiency is substantially identical, whether the waving lotion is formed from separate components or by reaction of acetylthiocholine with cysteine to form thiocholine and N-acetylcysteine in-situ, as shown in FIG. 1. The waving protocol used to collect the waving efficiency data contained herein was as follows:

PROCEDURE

1. Cut tresses into 0.67 gram samples (⅓ tresses).
2. Wet hair for 5 seconds in 100 ml beaker of 32° C. tap water.
3. Comb through hair with a small tooth comb to separate strands.
4. Fold end papers equally over the hair and spray with bottle of water.
5. Smooth end paper and place rod underneath.
6. Wrap hair with rod and secure with rubber clip of the rod at 0.25 inch above plastic tab.

7. Wet hair in 32° C. tap water for five seconds.

8. Towel blot well until no excess water remains.

9. Apply 750 ul of perm solution for 1/3 tresses—apply slowly and evenly over the tress inside the plastic cap. Up to 24 tresses of the same treatment may be placed into one bag. Do not mix sample treatments.

10. Flatten and close plastic cap with small binder clip and place it on either of the top two shelves of the 40° C. (±1° C.) oven. Convention is to move from left to right and top to bottom inside the oven. Start timer for 20 minutes or other specified time.

11. Rinse each tress for 30 seconds with 38° C. water at constant flow. Time and temperature are crucial in obtaining reproducible results.

12. After rinsing all tresses, towel blot well.

13. Neutralize tresses with 1000 ul of 2.2% hydrogen peroxide in a new plastic cap.

14. Place the cap into the 40° C. oven and process for 6 minutes.

15. Remove the tresses from the oven and rinse for 30 seconds as in step 11.

16. Towel blot all tresses.

17. Spiral unwrap (not conventional unwrap) tresses and carefully towel blot well.

18. Equilibrate samples in 65% relative humidity and 25° C. at least 3 hours or overnight.

19. Measure length of tress and calculate waving efficiency (percent shortening). $L_p$=length in cm of permed tresses; $L_o$=initial length of tress (15.2 cm).

$$\text{Wave Efficiency \%} = \frac{(L_o - L_p)}{L_o} (100)$$

These data indicate that the excess cysteine present in the waving lotion, when the thiocholine and N-acetylcysteine are formed in-situ by the reaction of acetylthiocholine and cysteine, does not provide additional reducing agent action at a neutral pH.

TABLE II

COMPARISON OF WAVING LOTION MADE FROM COMPONENTS VERSUS WAVING LOTION FORMED IN-SITU

| Wave | Thiocholine | N-acetylcysteine | Cysteine | Wave Efficiency |
|---|---|---|---|---|
| In-situ | 0.73M | 0.73M | 0.37M | 25.44 |
|  | 0.73M | 0.73M | 0.37M | 24.12 |
| Components | 0.73M | 0.73M | 0 | 25.88 |

Figure 4:
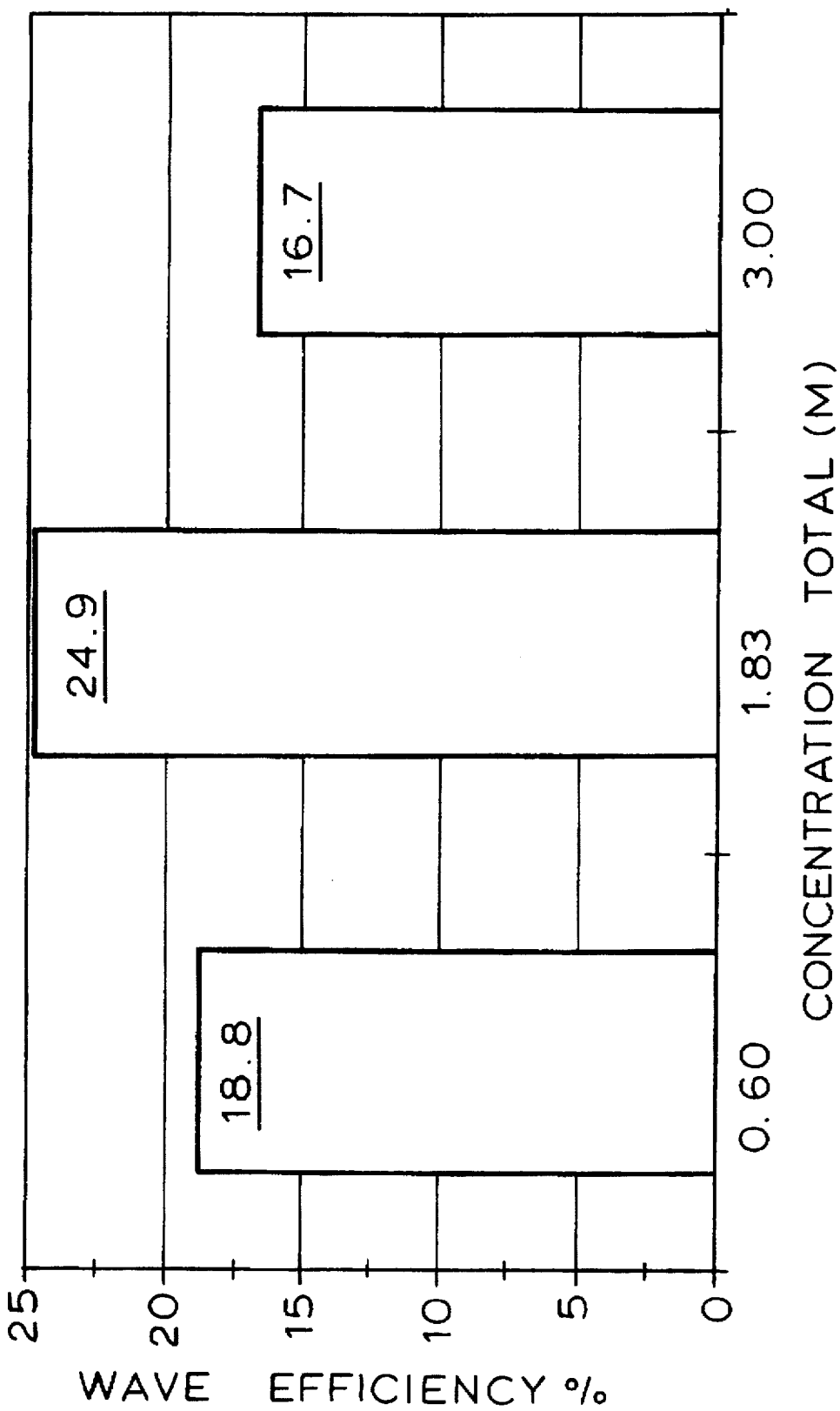
FIG. 4 is a bar graph showing waving efficiencies of the thiocholine/N-acetylcysteine combinations of one embodiment of the present invention at various equimolar concentrations (taken from Examples 1–3), with the graph showing total concentration of both components.
Figure 5:
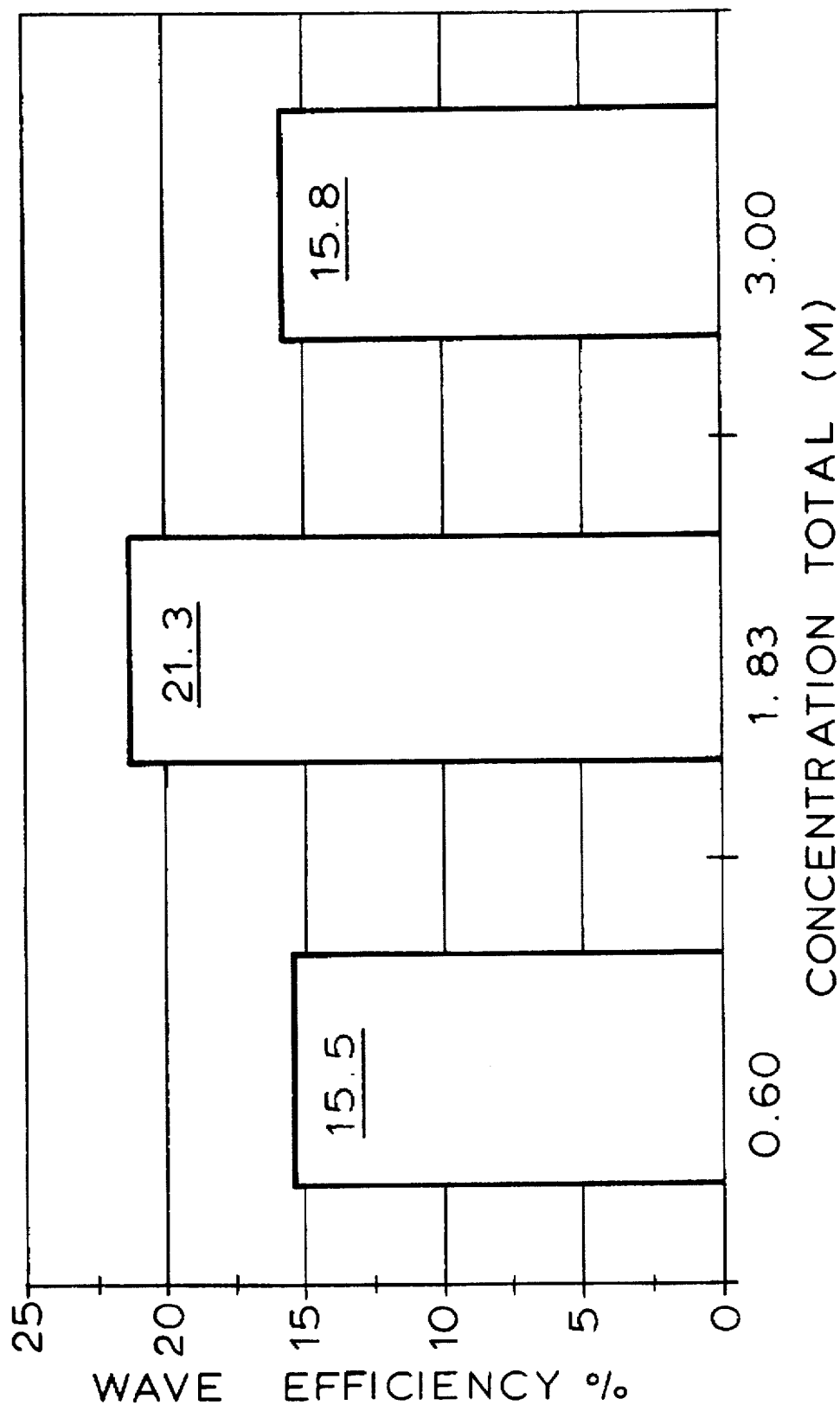
FIGS. 5 and 6 are graphs similar to FIG. 4 showing the wave efficiencies of the formulations of Examples 1–3 after one and three washes, respectively.
Figure 6:
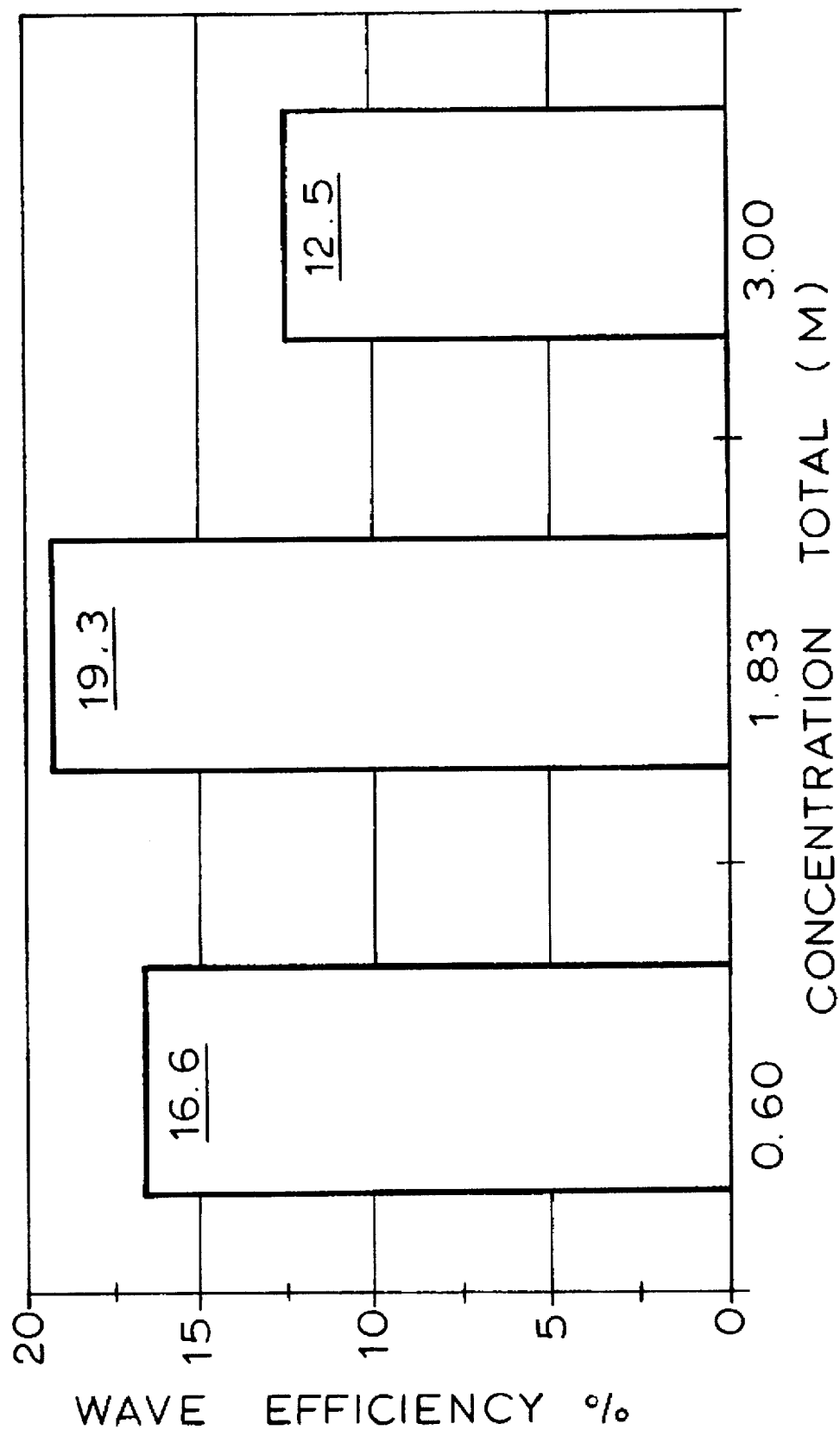

In order to determine optimum concentrations of thiocholine and N-acetylcysteine, three formulations were prepared (Examples 1–3) containing different concentrations of acetylthiocholine and cysteine hydrochloride, for in-situ reaction, forming thiocholine and N-acetylcysteine. As shown in the following Examples 1–3 and in FIGS. 4–6, the best waving efficiency was obtained at concentrations of thiocholine and N-acetylcysteine at 0.73M for each component.

EXAMPLES 1–3

| Example | Acetylthiocholine molar concentration | Cysteine Hydrochloride molar concentration | Wave Efficiency | Wave Efficiency 1× Wash | Wave Efficiency 3× Wash |
|---|---|---|---|---|---|
| 1 | 0.73M | 1.1M | 24.89 | 21.27 | 19.30 |
| 2 | 0.3M | 0.3M | 18.75 | 15.46 | 16.56 |
| 3 | 1.5M | 1.5M | 16.67 | 15.79 | 12.50 |

FORMULATIONS

| | EXAMPLE 1 | | EXAMPLE 2 | | EXAMPLE 3 | |
|---|---|---|---|---|---|---|
| Components | wt. % | grams | wt. % | grams | wt. % | grams |
| Deionized Water | 65.28 | 130.57 | 87.31 | 8.76 | 45.95 | 4.62 |
| Borax | 1.0 | 2.0 | 0.99 | 0.09 | 0.92 | 0.09 |
| L-cysteine | 13.35 | 26.70 | 3.61 | 0.36 | 16.73 | 1.67 |
| NaOH (50% active) | 5.91 | 11.82 | 2.19 | 0.21 | 9.10 | 0.90 |
| Acetylthiocholine Chloride | 14.46 | 28.91 | 5.90 | 0.58 | 27.30 | 2.72 |
| pH | 7.25 | | 7.4 | | 7.0 | |

Manufacturing Steps: Add Borax to deionized water and then add cysteine. Add NaOH to pH 9.15, then add acetylthiocholine and mix for 30 minutes. Adjust final pH by addition of NaOH.

The hair treated with the composition of Example I was tested for "post-perm" odor using the following protocol, and found to have essentially no "post-perm" odor, and less odor than cysteamine:

PROCEDURE

Preparation of 0.73M Cysteamine Wave Lotion

1. After adding stir bar, weigh 84.50 grams deionized water.
2. Weigh 11.00 grams cysteamine hydrochloride directly into beaker and stir gently.
3. Add 2.50 grams ammonium hydroxide carefully.
4. Add 2.00 grams ammonium bicarbonate and mix well.
5. insert pH probe and adjust pH if necessary with ammonium hydroxide to pH 8.3±0.04.
6. Store in opaque bottle.

Preparation of 2.2% Hydrogen Peroxide Neutralizer

1. In plastic beaker, weigh 93.76 grams deionized water. Add 6.23 grams hydrogen peroxide. Cover with foil due to light sensitivity.

Adjust pH with 0.004% phosphoric acid to pH 3.3–3.6.

Processing of Tresses

1. Apply 2×1000 ul of cysteamine wave lotion across each tress and place into plastic processing cap. Close cap with small binder clip and process for 20 minutes at 38° C.
2. Rinse tresses for 60 seconds with 38° C. tap water.
3. Towel blot tresses until no water spots appear.
4. Apply 2×1000 ul of a 2.2% hydrogen peroxide neutralizer, pH 3.5 and process 5 minutes inside plastic wave cap at 38° C.
5. Rinse tresses for 60 seconds at 38° C. with tap water and place on paper towel.
6. After spraying tress 10 times with deionized water, insert tress into glass jar and incubate at 50° C. overnight. If performing a time study, the tresses should be dried before incubating in the oven. This is done to help prevent microbiological growth.
7. Tresses are next rewetted in 50° C. water for an odor panel or ready for further performance testing.

The hair treated with the compositions of all Examples 1–9 were checked for smell at all stages of permanent waving, and no odor problems were detected which might indicate that a "post-perm" odor would develop.

Additional formulations were prepared similar to those of Examples 1–3 using separate components of thiocholine and N-acetylcysteine at concentrations of each component ranging from 0.50M to 1.30M to confirm the optimum concentrations of each component. Again, the optimum concentration for both thiocholine and N-acetylcysteine was at a molar concentration of 0.73, as shown in Table III.

TABLE III

EFFECT OF MOLAR CONCENTRATION ON WAVING EFFICIENCY AT PH 7.0

| | Molar Concentration | | |
|---|---|---|---|
| Example | Thiocholine | N-acetylcysteine | Wave Efficiency |
| 4 | 0.50 | 0.50 | 17.76 |
| 5 | 0.73 | 1.10 | 29.72 |
| 6 | 1.10 | 1.30 | 22.26 |
| 7 | 1.30 | 1.30 | 23.25 |

Figure 7:
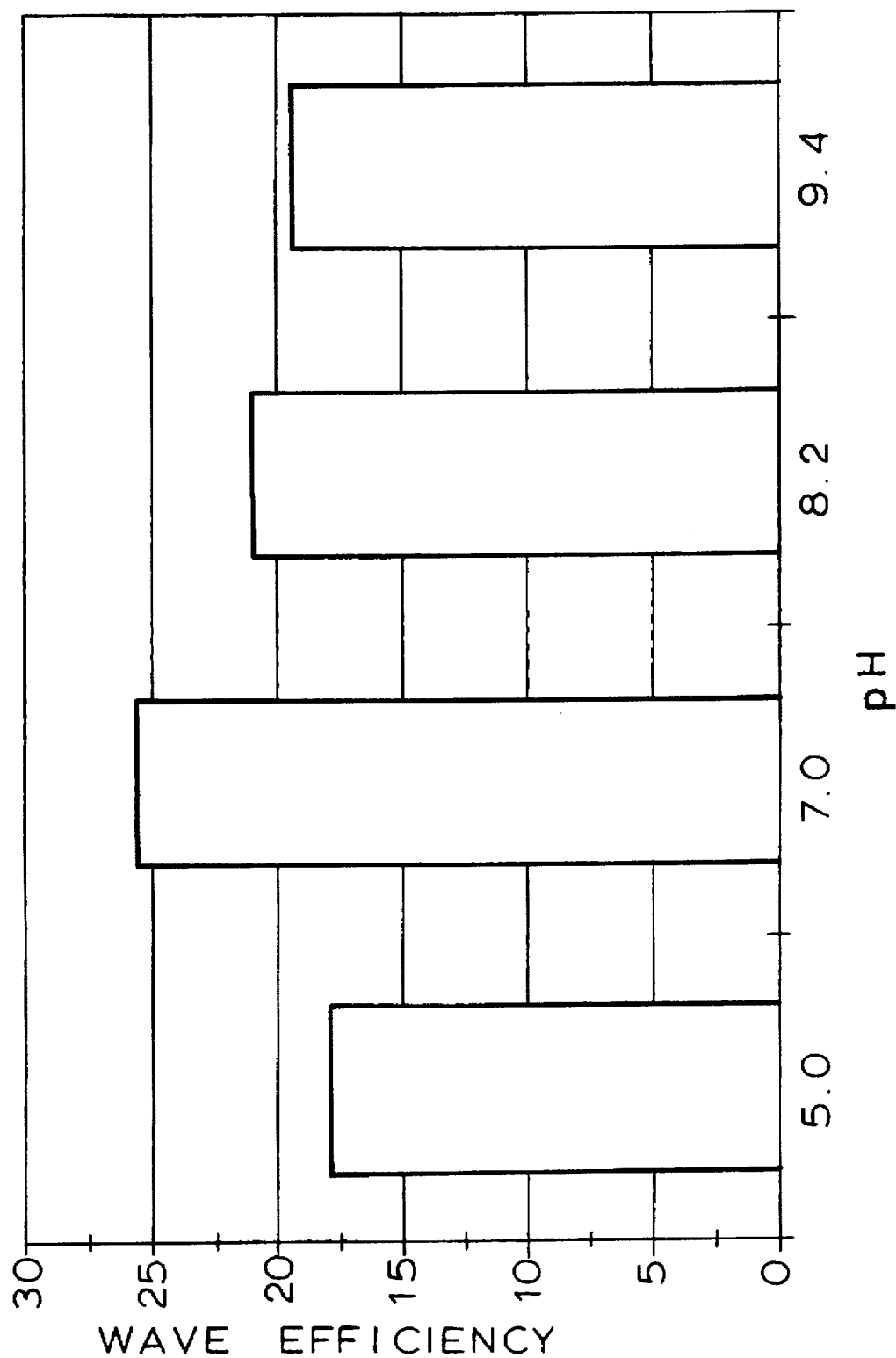
FIG. 7 is a bar graph showing the waving efficiencies of 0.73M thiocholine and 0.73M N-acetylcysteine at various pHs.

In order to determine an optimum pH for the waving lotion composition of the present invention, four different compositions containing the preferred concentrations of 0.73M thiocholine and 0.73M N-acetylcysteine were prepared at pHs of 5.0, 7.0, 8.2 and 9.4. The data of Table IV and FIG. 7, show that waving efficiency is best at a neutral pH of about 7.0.

TABLE IV

EFFECT OF PH

| pH | Waving Efficiency |
|---|---|
| 5.0 | 18.0 |
| 7.0 | 25.7 |
| 8.2 | 21.1 |
| 9.4 | 19.5 |

The following formulation of Example 8 was prepared to confirm that the reducing agent composition of the present invention containing thiocholine and N-acetylcysteine is effective as a hair straightening agent for curly hair.

EXAMPLE 8

| DESCRIPTION | WEIGHT % | GRAMS |
|---|---|---|
| Water, deionized | 65.23 | 65.23 |
| Borax | 1.00 | 1.00 |
| L-cysteine | 13.36 | 13.35 |
| Sodium Hydroxide, Liquid 50% | 5.96 | 5.95 |
| Acetylthiocholine Chloride | 14.45 | 14.45 |

Manufacturing Steps:
1. Add Borax to deionized water.
2. Add cysteine.
3. Add NaOH to pH 9.15, such that cysteine dissolves fully.
4. Add acetylthiocholine and mix 30 minutes
5. Final pH 7.25 to 7.5 by addition of NaOH.

The following procedure was used to test the formulation of Example 8 as a hair straightening lotion.

PROCEDURE

Negro hair was tressed onto tabs, dried four hours, and combed with a "pic" before the straightening process.

1. The tresses were washed with deionized water and shampooed using 0.46 ml SUAVE® shampoo two times.
2. 470 ml wave lotion was then applied and combed through the hair for five minutes.
3. Tresses were then placed in oven at 38° C. for 20 minutes. Time of process, total, was 25 minutes.
4. The tresses then were rinsed for 30 seconds with 38° C. tap water and blotted.
5. The tresses then were neutralized with 470 ml of 2.2% $H_2O_2$ for five minutes at 38° C.
6. The tresses were then rinsed for 30 seconds and blotted.
7. The tresses were then hung at room temperature (25° C.) and 40% relative humidity.
8. Measured tressed: DI $H_2O$ (control) versus formulation of Example 8.

| | INITIAL (cm) | FINAL (cm) |
|---|---|---|
| Example 8 | 9.0 | 13.6 |
| Control | 9.0 | 8.8 |

Example 8 formulation lengthening = 51.11%
Control lengthening = −2.2%

In addition to the effective hair straightening, the hair also felt softer and in better condition than prior to treatment with the straightener.

The proposed theory of ionic complexing between the anionic and cationic compounds, in solution, was confirmed by both nuclear magnetic resonance (NMR) and infrared (IR) testing of solutions containing the cationic compound alone and the anionic compound alone in comparison to both the cationic compound and the anionic compound in solution together. The cationic and anionic compounds tested, with significant carbons numbered, were thiocholine and N-acetylcysteine, as follows:

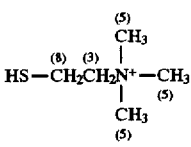

Thiocholine

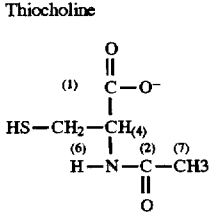

N-acetylcysteine

Figure 9:
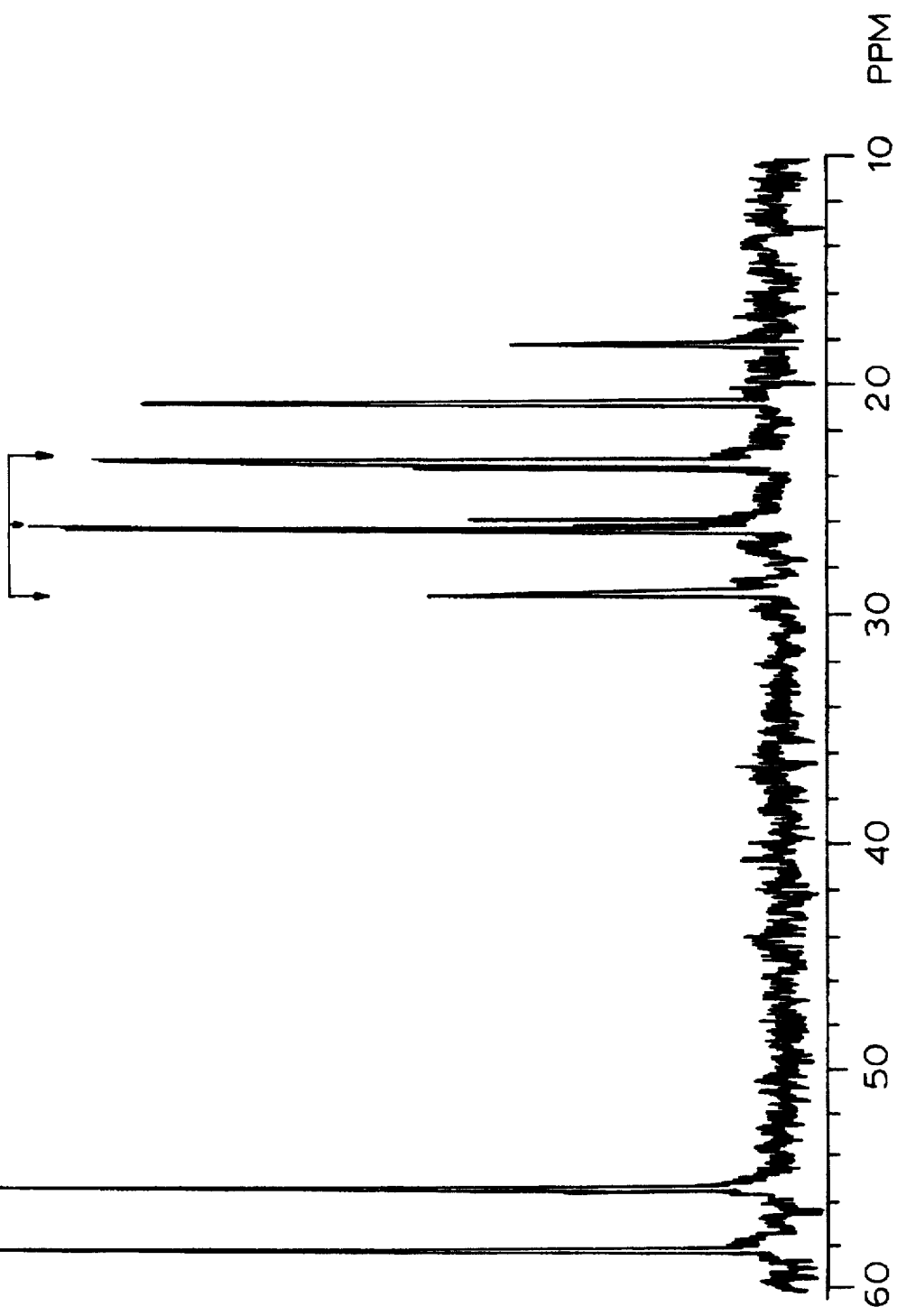
FIGS. 9–11 are NMR graphs showing the proton-coupled C13 chemical shifts for aqueous solutions of N-acetylcysteine (FIG. 9), thiocholine (FIG. 10) and the combination of thiocholine and N-acetylcysteine, at concentrations of 0.73M for each component at a pH of 7.0. It should be noted that the scale for FIG. 10 is different from the scale of FIGS. 9 and 11.
Figure 10:
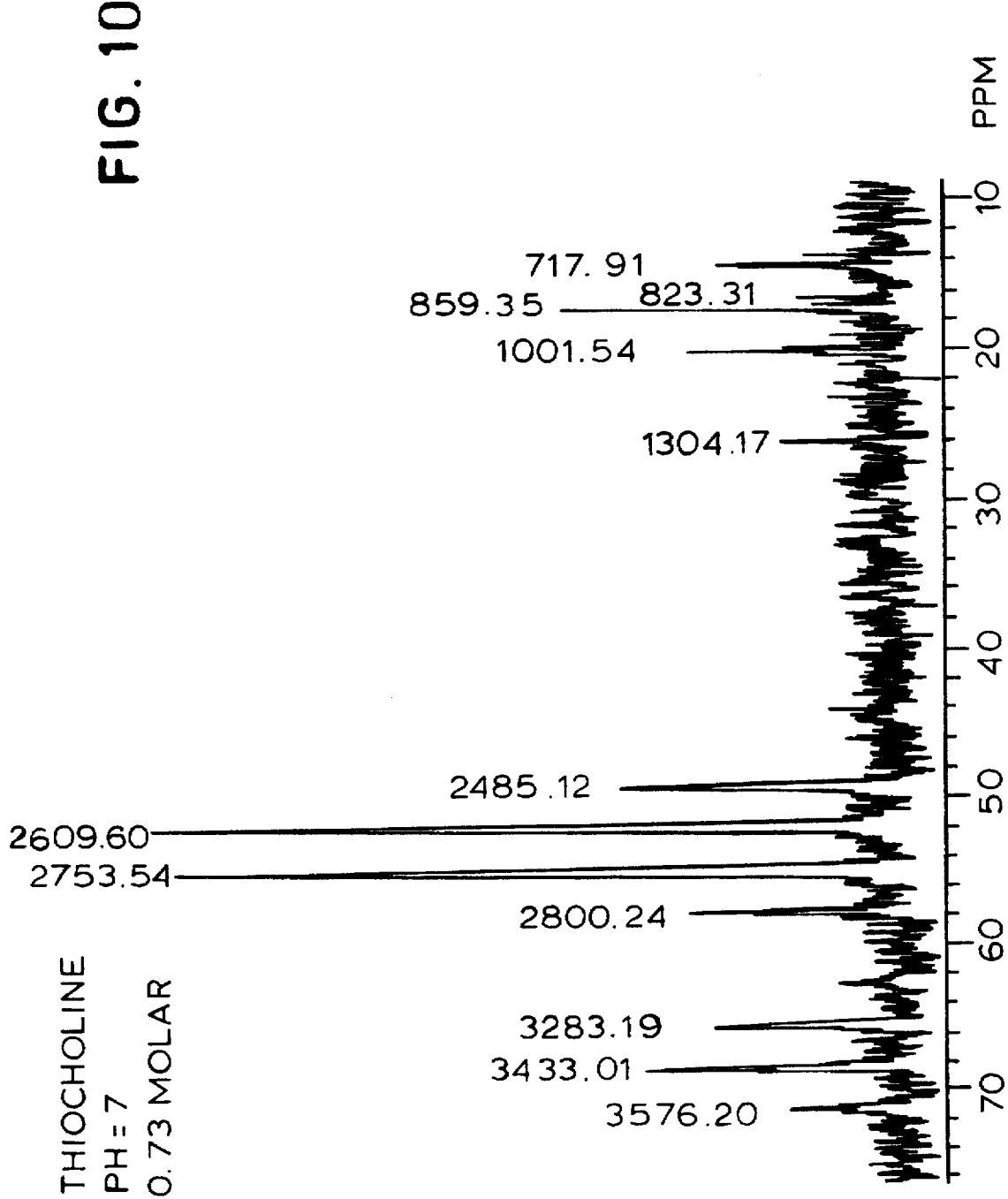
Figure 11:
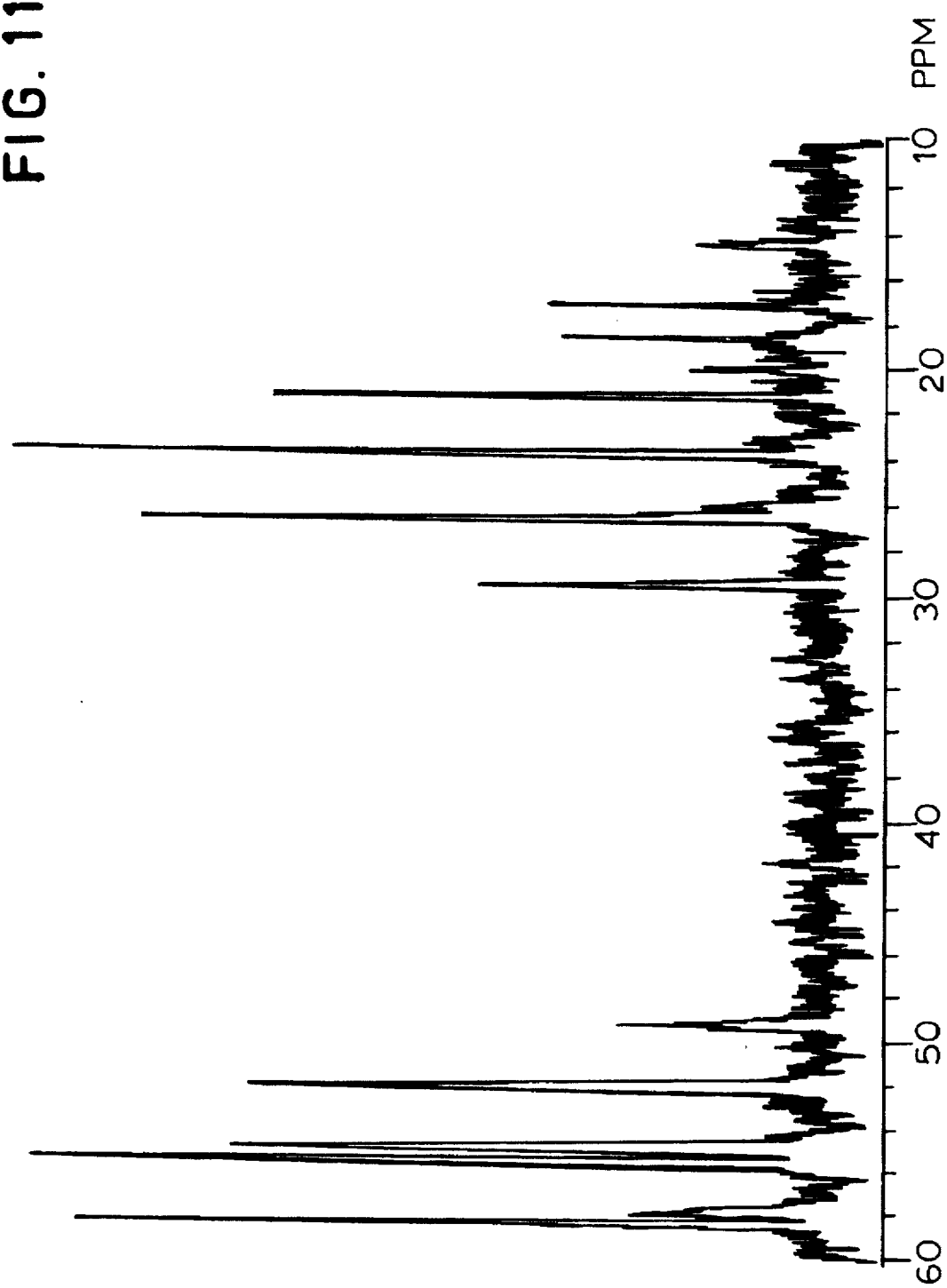

Table V and FIGS. 9–11 provides NMR data for proton decoupled C13 chemical shifts in parts per million (ppm) for aqueous solutions of thiocholine, N-acetylcysteine and a mixture of thiocholine and N-acetylcysteine, each component at 0.73M concentration, and a pH of 7.0.

TABLE V

SUMMARY OF C13 PPM VALUES FOR THIOCHOLINE N-ACETYLCYSTEINE

| Sample | pH | NAC C=O (1) | NAC C=O (2) | TC —CH$_2$— (3) | NAC —CH (4) | TC —NCH$_3$ (5) | NAC —SCH$_2$ (6) | NAC —CH$_3$ (7) | TC —SCH$_2$ (8) |
|---|---|---|---|---|---|---|---|---|---|
| Thiocholine | 9 | | | 70.37 | | 53.4, 53.0 | | | 16.98 |
| | 7 | | | 68.23 | | 53.33 | | | 17.09 |
| | 3 | | | 67.97 | | 53.39 | | | 17.14 |
| N-acetylcysteine | 9 | 176.54 | 173.54 | | 59.92 | | 26.33 | 21.99 | |
| | 7 | 176 | 173 | | 56.67 | | 26.23 | 21.94 | |
| | 3 | 173.82 | 173.70 | | 54.84 | | 25.20 | 21.60 | |
| Thiocholine/ | 9 | 176.56 | 173.51 | 69.67 | 57.14 | 53.36 | 26.72 | 22.73 | 17.28 |
| N-acetylcysteine | 7 | 176.32 | 173.48 | 68.33 | 58.83 | 53.34 | 26.55 | 22.46 | 17.13 |
| | 3 | 174.49 | 173.66 | 67.89 | 55.61 | 53.43 | 25.94 | 22.38 | 17.21 |

TC = Thiocholine
NAC = N-acetylcysteine

The proton decoupled C13 chemical shifts in ppm for thiocholine, N-acetylcysteine and the thiocholine/N-acetylcysteine mixture are presented in Table V. Of particular interest is the significant shift for the mixture of thiocholine and N-acetylcysteine to higher field of the carbons Alpha, and Beta to the sulfur in N-acetylcysteine, relative to N-acetylcysteine at all pH's (columns 6, 7). These shifts are indicative of delocalization of electrons away from these two carbons resulting from the formation of a complex between the thiocholine and N-acetylcysteine. Further evidence for this interaction can be found in the proton coupled spectra of FIG. 9. In the spectra of N-acetylcysteine at pH 7, the triplet assigned to this carbon (6) is split while in the mixture it is free. Similar results are observed at pH 9, but splitting is not observed in the pH 3 sample where the carboxyl group is protonated and not available for hydrogen bonding. For thiocholine, the absorption assigned to the methyl carbon is split in the pH 9 sample; this splitting disappears in the mixture (column 5).

These data are consistent with infrared (IR) data for the same samples in which the SH group shows a wide band in N-acetylcysteine and a narrow band in the mixture. This behavior is indicative of strong hydrogen bonding between the thiol cation of thiocholine and the carboxylate anion of N-acetylcysteine.

Figure 12:
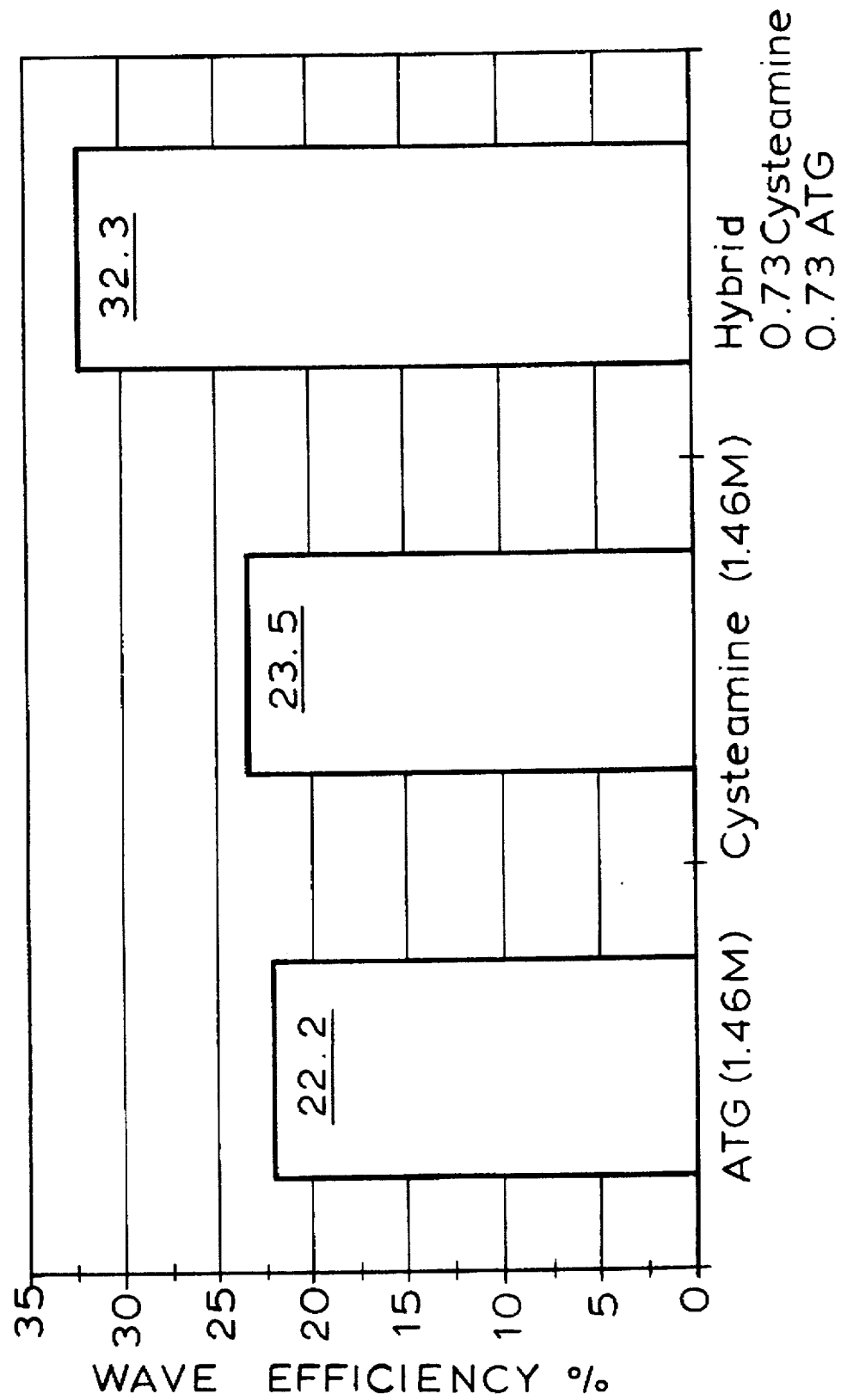
FIGS. 12–14 are bar graphs showing the waving efficiencies of a combination of a thioglycolic acid salt (ammonium thioglycolate) together with cysteamine, at a pH of 6.5, compared to ammonium thioglycolate or cysteamine alone, and showing the waving efficiencies after one and three washings.

The following formulations of Examples 9–11 (graphed in FIG. 12), were prepared to show the synergistic effect of a combination of ammonium thioglycolate (anion) and cysteamine (cation) at a pH of about 6.5, in comparison to each compound alone.

| WAVING EFFICIENCY OF ATG/CYSTEAMINE HYBRID AT PH 6.5 | | | |
|---|---|---|---|
| Component | Example 9 (wt. %) | Example 10 (wt. %) | Example 11 (wt. %) |
| deionized water | 82.10 | 87.46 | 71.13 |
| ammonium thioglycolate (60% active) | 16.67 | 0.00 | 16.67 |
| cysteamine HCl (75% active) | 0.00 | 11.00 | 11.00 |
| Borax | 1.00 | 1.00 | 1.00 |
| phosphoric acid | 0.23 | 0.54 | 0.20 |
| (85% active) | | | |
| total | 100.00 | 100.00 | 100.00 |
| pH | 6.5 | 6.5 | 6.5 |

Figure 8:
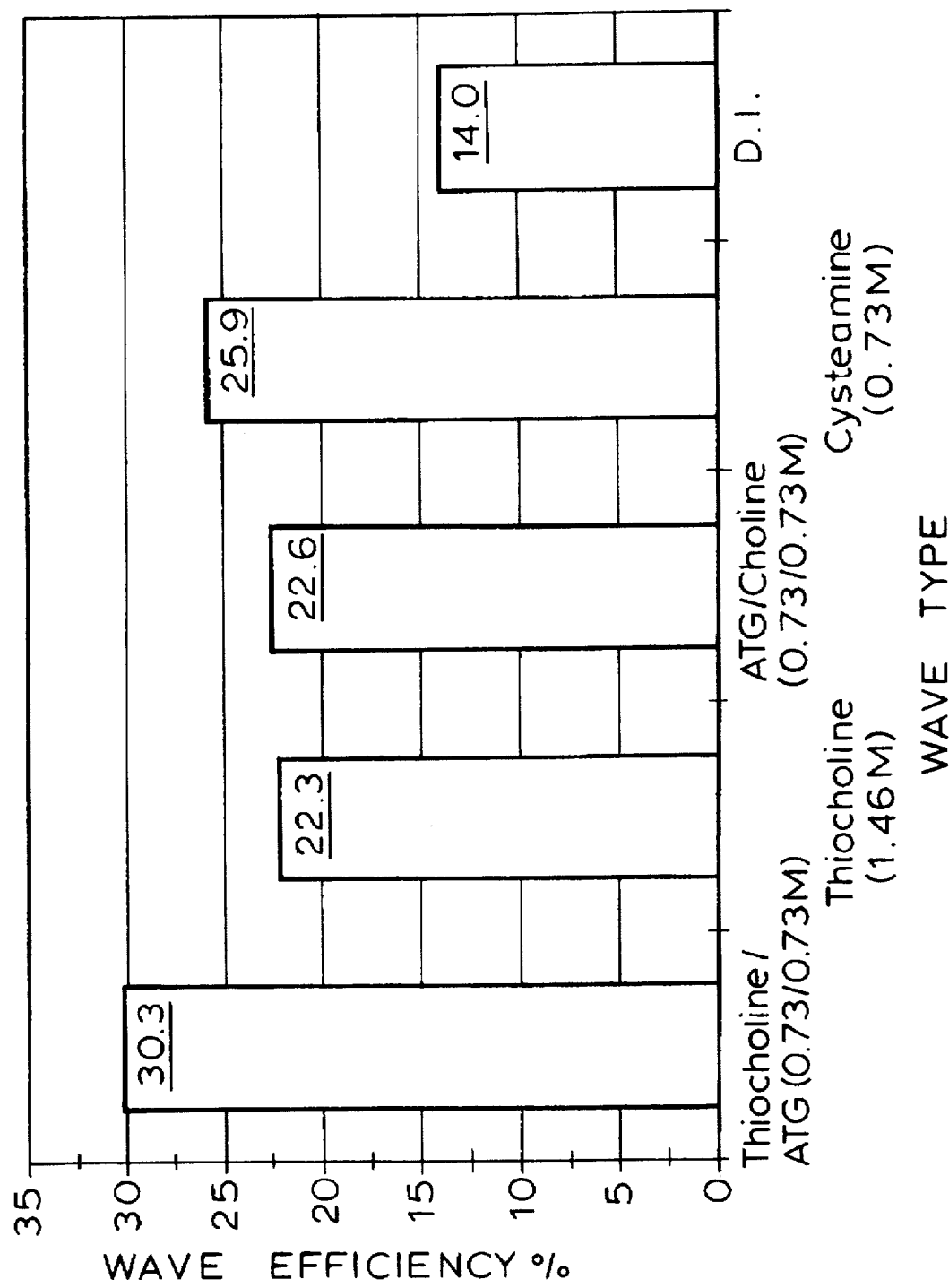
FIG. 8 is a bar graph showing the waving efficiencies of another ionic pair in accordance with the present invention (thiocholine and ammonium thioglycolate) compared to thiocholine above, cysteamine above, and a combination of choline and ammonium thioglycolate, with deionized water as a control.
Figure 13:
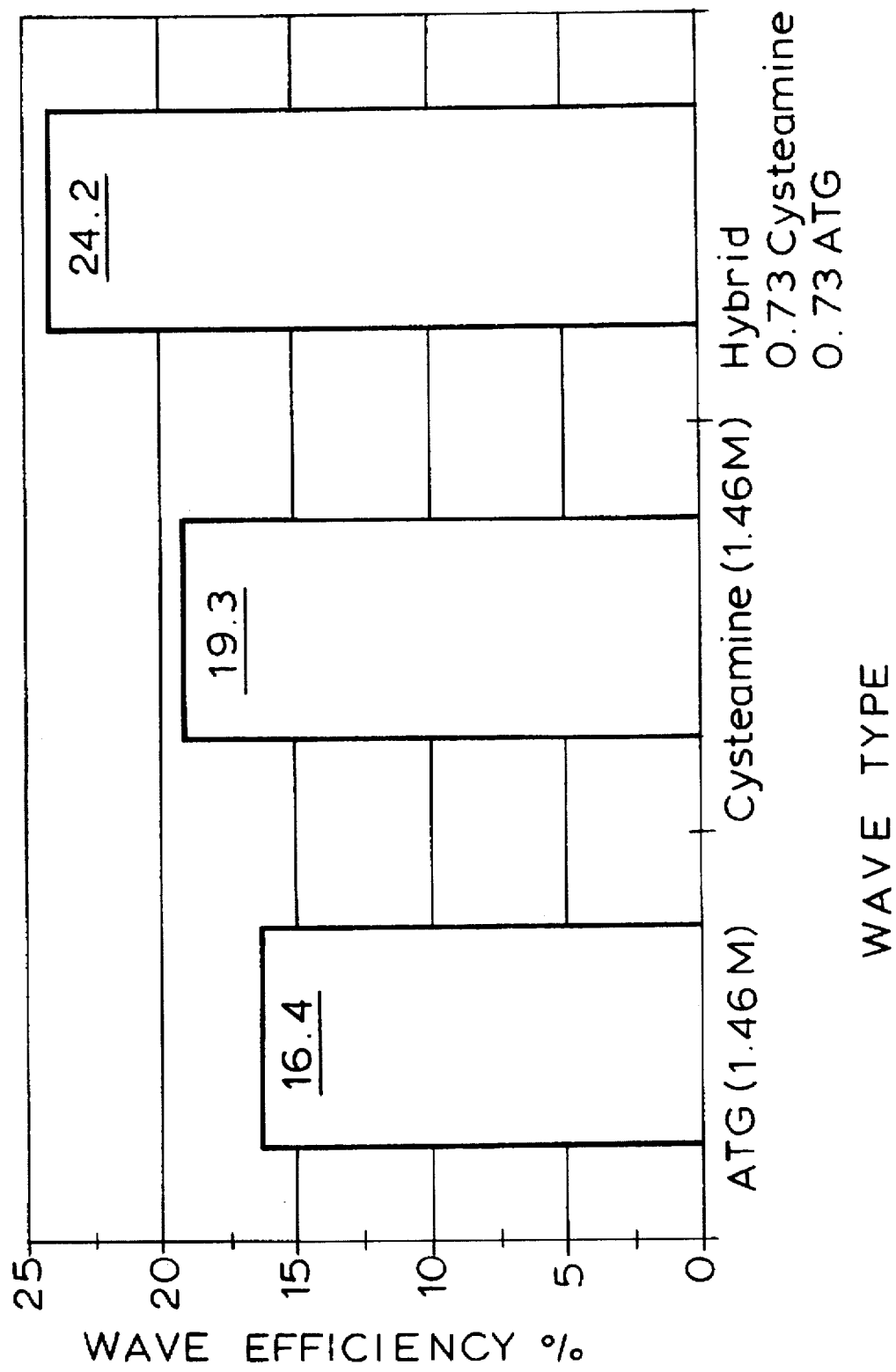
Figure 14:
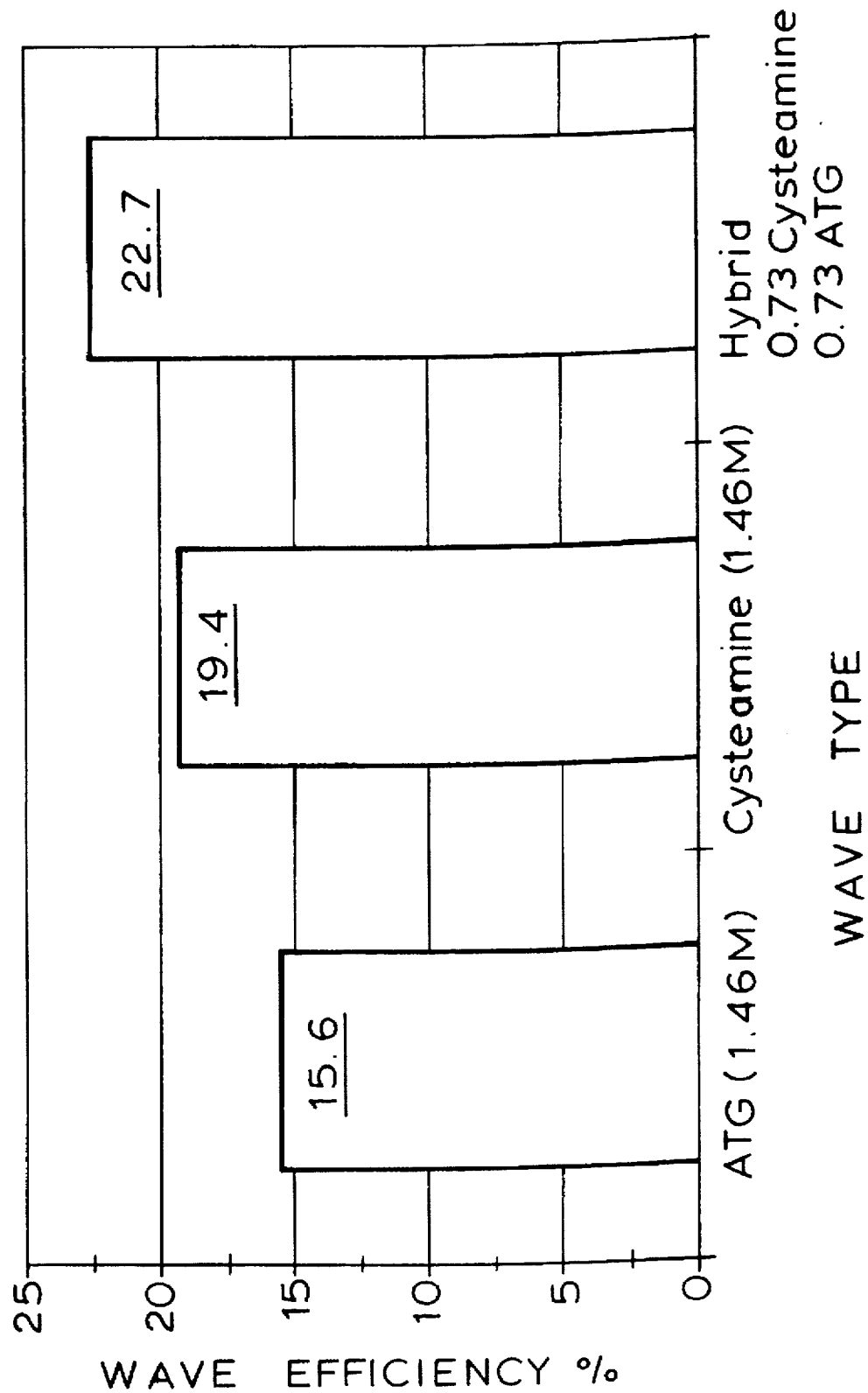

The waving efficiencies of the formulations of Examples 9–11 were then measured after 1 and 3 washes and the waving efficiencies graphed in FIGS. 13 and 14, respectively. Quite unexpectedly, it was found that the waving efficiencies for combinations of thioglycolic acid or a salt of thioglycolic acid, e.g., ammonium thioglycolate, as the anion, together with a cation disclosed herein, e.g., thiocholine (FIG. 8) or cysteamine (Example 9 and FIGS. 12–14), provide synergistic waving efficiencies, surprisingly at a pH below 9.0, due to the formation of an anionic-cationic complex formed in solution. It was most surprising that these waving efficiencies were obtained at a pH below 7.0.

Figure 15:
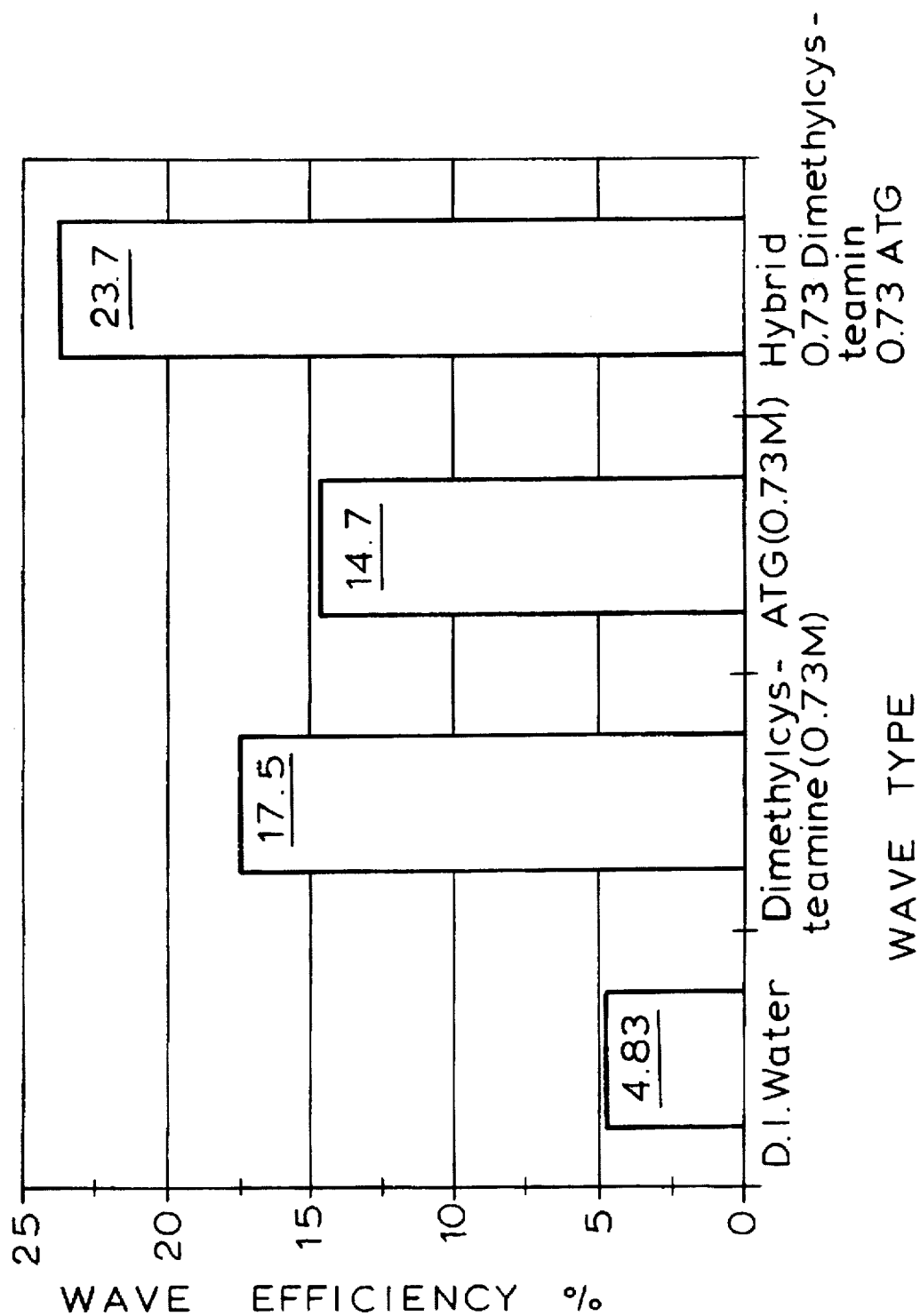
FIGS. 15 and 16 are bar graphs showing synergistic waving efficiencies of a combination of a thioglycolic acid salt (ammonium thioglycolate) together with dimethylcysteamine at pHs of 5.0 to 9.5, compared to deionized water, cysteamine, and each component alone.
Figure 16:
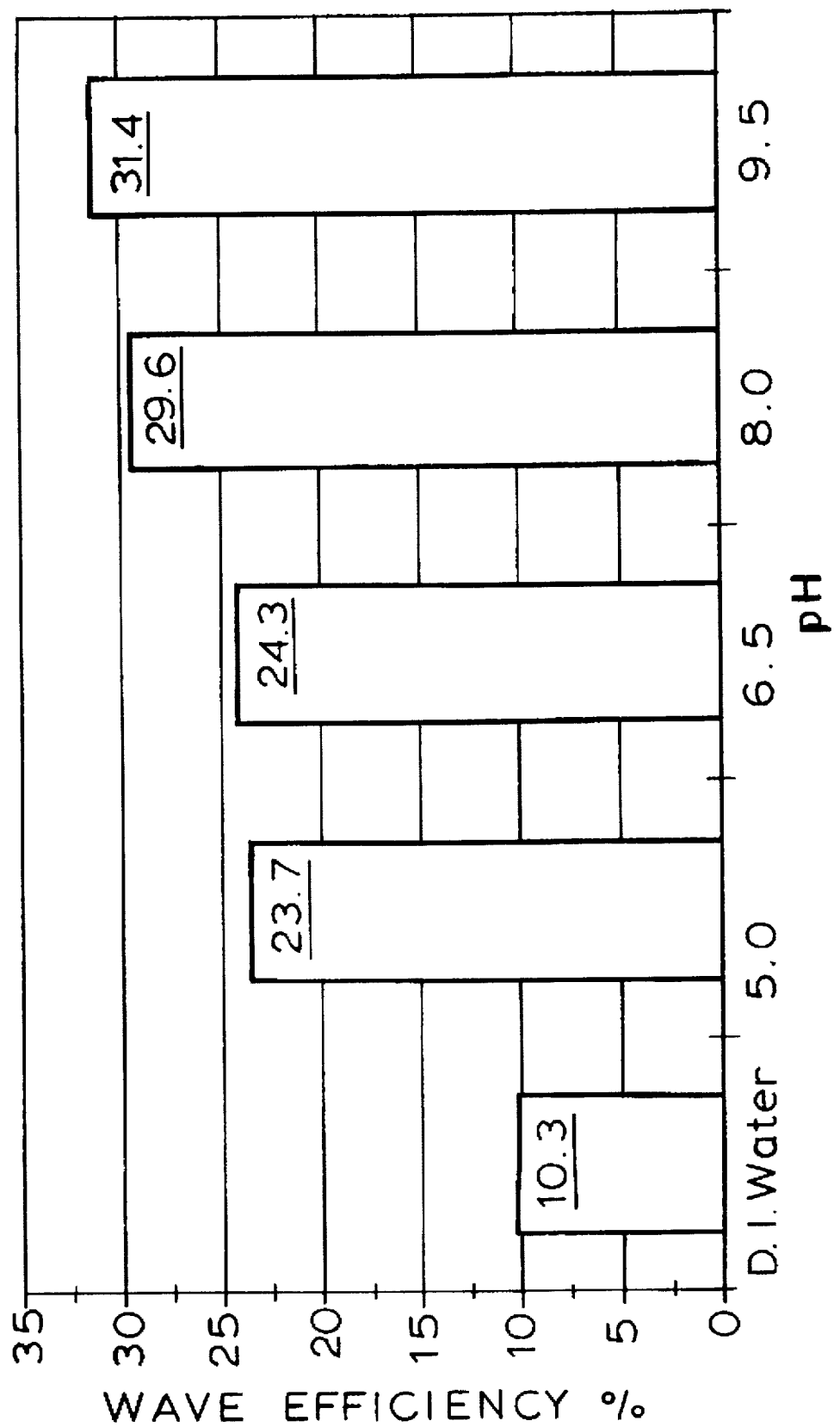

The waving efficiencies of alkylated cysteamine, particularly dimethylcysteamine, together with ammonium thioglycolate at various pHs at component concentrations of 0.73M were studied in comparison to deionized water, cysteamine and in comparison to ammonium thioglycolate and dimethylcysteamine alone, as shown by the data of Tables VI and VII used to form FIGS. 15 and 16, respectively.

TABLE VI

WAVING EFFICIENCY OF DIMETHYLCYSTEAMINE AND ATG AT VARIOUS PHs

| Component | pH | Molar Concentration | Wave Efficiency |
|---|---|---|---|
| Deionized water | 7.0 | — | 4.83 |
| Ammonium thioglycolate | 5.0 | 0.73M | 14.69 |
| Dimethylcysteamine | 5.0 | 0.73M | 17.54 |
| Dimethylcysteamine/Ammonium thioglycolate | 5.0 | 0.73M/0.73M | 23.68 |

TABLE VII

WAVING EFFICIENCY OF DIMETHYLCYSTEAMINE AND ATG AT VARIOUS PHs

| Component | pH | Molar Concentration | Wave Efficiency |
|---|---|---|---|
| Deionized water | 7.0 | — | 10.31 |
| Cysteamine | 8.3 | 0.73M | 25.66 |
| Dimethylcysteamine/Ammonium thioglycolate | 5.0 | 0.73M/0.73M | 23.68 |
| Dimethylcysteamine/Ammonium thioglycolate | 6.5 | 0.73M/0.73M | 24.34 |
| Dimethylcysteamine/Ammonium thioglycolate | 8.0 | 0.73M/0.73M | 29.61 |
| Dimethylcysteamine/Ammonium thioglycolate | 9.5 | 0.73M/0.73M | 31.36 |

As shown in the data of Tables VI and VII and in FIGS. 15 and 16, the combinations of dimethylcysteamine and ammonium thioglycolate provided synergistic wave efficiencies compared to each component alone, over the full range of pHs studied.

Figure 18:
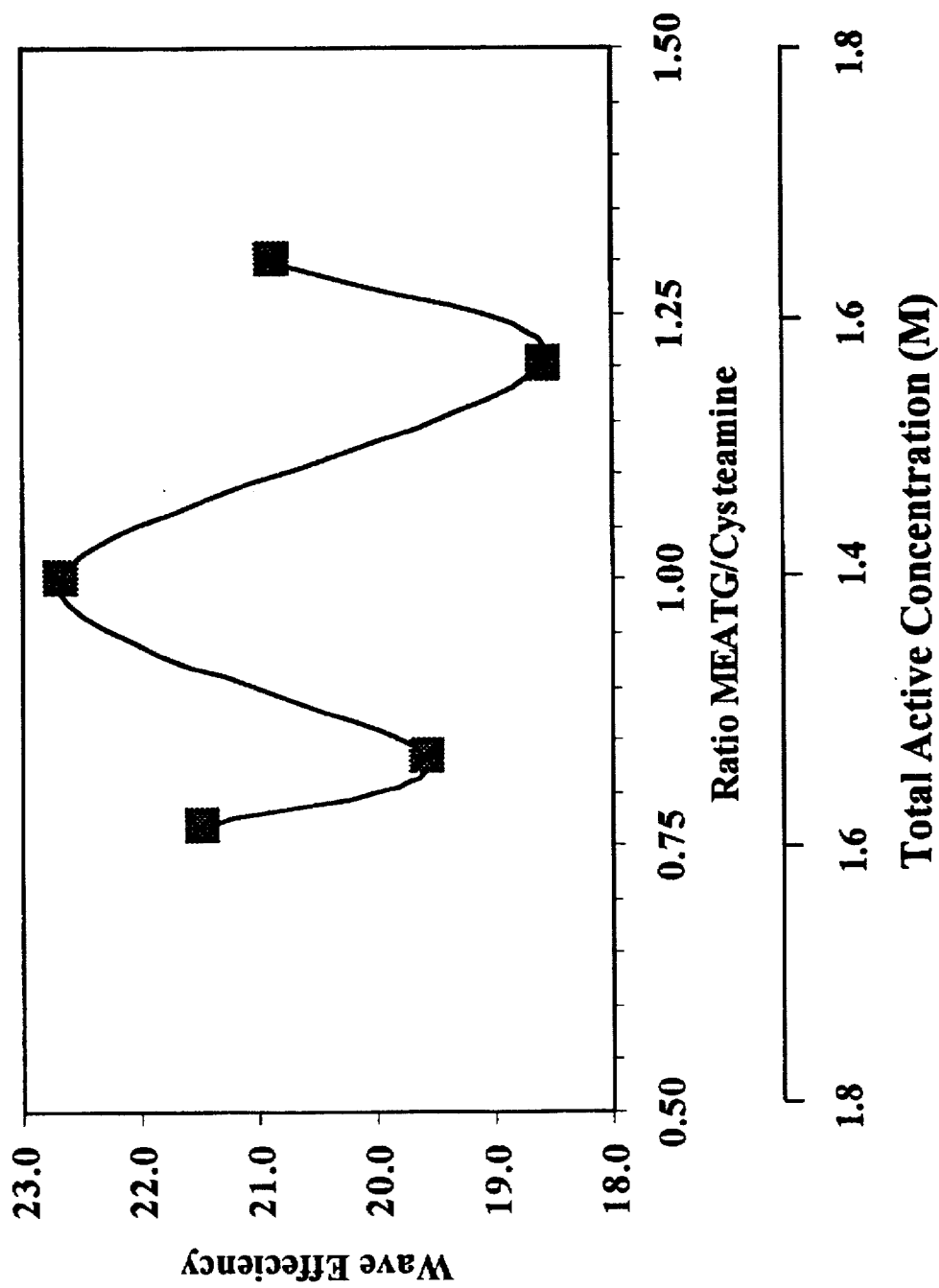
FIG. 18 is a graph showing the wave efficiencies of solutions of cationic cysteamine and anionic monoethanolamine thioglycolate (MEATG) at various molar ratios of MEATG:cysteamine over the range of 1.3:1 to 1:1.3, at pH 7.0, showing total molar concentrations of cationic and anionic compounds.

The waving efficiencies of cysteamine HCl and monoethanolamine thioglycolate (MEATG) at pH 7.0 and over a range of molar ratios of 1:1.3 to 1.3:1 were studied in comparison to a deionized water (DI) control to determine the molar ratios of cationic compound to anionic compound for best waving efficiency. As shown by the following examples 12–16, and the summary of data provided in Table VIII, and FIG. 18, cationic/anionic complexing occurs over the molar ratio of cationic compound to anionic compound in the range of about 1:1.2 to about 1.2:1, and best waving efficiency occurs over the molar ratio of about 1:1.1 to about 1.1:1.

| Ingredient | Weight % |
|---|---|
| Example 12 | |
| 0.73M MEATG/Cysteamine Hybrid, pH 7.0 | |
| Ratio 1 to 1 MEATG: Cysteamine | |
| Water, Deionized | 64.72 |
| Tetrasodium EDTA (Versene 100) | 0.51 |
| Sodium Dihydrogen Phosphate | 2.50 |
| Cysteamine.HCL, 75% (aq) | 11.00 |
| MEA Thioglycolate, 40% as TG | 16.81 |
| Monoethanolamine | 1.27 |
| PEG-15 Nonyl Phenyl Ether | 2.50 |
| Fragrance | 0.70 |
| Example 13 | |
| 0.73M MEATG/0.88M Cysteamine Hybrid, pH 7.0 | |
| Ratio 1 to 1.21 MEATG: Cysteamine | |
| Water, Deionized | 62.17 |
| Tetrasodium EDTA (Versene 100) | 0.51 |
| Sodium Dihydrogen Phosphate | 2.50 |
| Cysteamine.HCL, 75% (aq) | 13.33 |
| MEA Thioglycolate, 40% as TG | 16.81 |
| Monoethanolamine | 1.48 |
| PEG-15 Nonyl Phenyl Ether | 2.50 |
| Fragrance | 0.70 |
| Example 14 | |
| 0.73M Cysteamine/0.88M MEATG Hybrid, pH 7.0 | |
| Ratio 1.21 to 1.00 MEATG: Cysteamine | |
| Water, Deionized | 60.92 |
| Tetrasodium EDTA (Versene 100) | 0.51 |
| Sodium Dihydrogen Phosphate | 2.50 |
| Cysteamine.HCL, 75% (aq) | 11.00 |
| MEA Thioglycolate, 40% as TG | 20.27 |
| Monoethanolamine | 1.50 |
| PEG-15 Nonyl Phenyl Ether | 2.50 |
| Fragrance | 0.70 |
| Example 15 | |
| 0.73M MEATG/0.949M Cysteamine Hybrid, pH 7.0 | |
| Ratio 1 to 1.30 MEATG: Cysteamine | |
| Water, Deionized | 61.25 |
| Tetrasodium EDTA (Versene 100) | 0.51 |
| Sodium Dihydrogen Phosphate | 2.50 |
| Cysteamine.HCL, 75% (aq) | 14.37 |
| MEA Thioglycolate, 40% as TG | 16.81 |
| Monoethanolamine | 1.36 |
| PEG-15 Nonyl Phenyl Ether | 2.50 |
| Fragrance | 0.70 |
| Example 16 | |
| 0.73M Cysteamine/0.949M MEATG Hybrid, pH 7.0 | |
| Ratio 1.30 to 1 MEATG: Cysteamine | |
| Water, Deionized | 59.37 |
| Tetrasodium EDTA (Versene 100) | 0.51 |
| Sodium Dihydrogen Phosphate | 2.50 |
| Cysteamine.HCL, 75% (aq) | 11.00 |
| MEA Thioglycolate, 40% as TG | 21.86 |
| Monoethanolamine | 1.56 |
| PEG-15 Nonyl Phenyl Ether | 2.50 |
| Fragrance | 0.70 |

TABLE VIII

WAVING EFFICIENCY OF MEATG AND CYSTEAMINE AT VARIOUS MOLAR RATIOS

| | | | | | ratio | | | | | | |
|---|---|---|---|---|---|---|---|---|---|---|---|
| | | | | | Waving Efficiency | | | | | | |
| Example No. | Molar Ratio | Avg. | 1 | 2 | 3 | 4 | 5 | 6 | St. Dev. | Min. | Max. |
| 12 | 1:1 MEA:Cys | 22.7 | 22.4 | 22.4 | 23.7 | 22.4 | 23.0 | 22.4 | 0.6 | 22.4 | 23.7 |
| Control | DI | 8.6 | 9.2 | 8.6 | 9.2 | 7.9 | 7.9 | 8.6 | 0.6 | 7.9 | 9.2 |
| 13 | 1:1.2 MEA:Cys | 19.6 | 21.1 | 21.7 | 21.1 | 17.8 | 18.4 | 17.8 | 1.8 | 17.8 | 21.7 |
| 14 | 1.2:1 MEA:Cys | 18.6 | 20.4 | 19.7 | 18.4 | 17.8 | 17.8 | 17.8 | 1.2 | 17.8 | 20.4 |
| 15 | 1:1.3 MEA:Cys | 21.5 | 20.4 | 20.4 | 21.1 | 23.0 | 22.4 | 21.7 | 1.1 | 20.4 | 23.0 |
| 16 | 1.3:1 MEA:Cys | 20.9 | 20.4 | 19.7 | 20.4 | 22.4 | 21.7 | 21.1 | 1.0 | 19.7 | 22.4 |

Preferably, the reducing composition also includes a hair moisturizer and/or softener selected from a polyhydroxyl alkyl compound, a polyalkylene glycol glycerol ether, an ethoxylated fatty alcohol, a fatty alcohol polymerized ether, and mixtures thereof in an amount of about 0.1% to about 20% by weight, particularly about 0.1% to about 15% by weight.

Optionally, the composition of the present invention includes a conditioner to improve the combing and manageability of the hair, such as the silicone conditioning agents well known in the art. The conditioner, when added, is included in an amount of about 0.01% to about 2.0% by weight of the composition.

Other common cosmetic additives can be incorporated into the composition of the present invention, as long as the additives do not form an ionic complex in solution with the cationic or anionic compounds of the present invention. These additives include, but are not limited to, commonly used fragrances, dyes, surfactants or solubilizers, opacifiers, pearlescing agents, thickeners, foam stabilizers, preservatives, water softening agents, acids, bases, buffers and the like; and will usually be present in weight percentages of less than about 1% each, and about 2% to about 5% in total. The composition vehicle is predominantly water but organic solvents also can be added to the composition in order to solubilize compounds that are not sufficiently soluble in water. Suitable solvents include the lower alcohols, such as ethanol and isopropanol and mixtures. These solvents can be present in the hair setting composition of the present invention in an amount from about 1% to about 75% by weight and in particular from about 5% to about 50% by weight, based on the total weight of the composition.

Cationic additives that will complex, in solution, with the anionic thiocarboxylate anion of the composition of the present invention will reduce the amount of the above-described cationic/anionic complex of the present invention, thereby reducing the waving efficiency of the waving lotion composition. Similarly, an anionic additive, such as a carboxylic acid, or carboxylate surfactant, reduces the waving efficiency of the waving lotion of the present invention. Such unwanted complexing can be compensated for by adding more of the anionic or cationic compound that is uselessly complexed to achieve the advantages of the present invention. However, such further additions of anionic or cationic components cause needless expense and, therefore, such unwanted complexes are best avoided.

For example, in the Japanese Showa Patent 57062217, it is disclosed that cysteamine and thioglycolic acid are effective together at a pH of 9.0. In this Showa patent, it appears that the inventors did not investigate cysteamine-thioglycolic acid mixtures at pH's other than 9.0. Additionally, the Showa inventors used citric acid for pH adjustment. As demonstrated in FIG. 17, citric acid interferes with the ionic complexing theory first disclosed herein. Thus, if the Showa inventors worked at pH's lower than 9.0, they would not have discovered the invention disclosed herein.

In accordance with the above-detailed ionic complexing theory discovered by Applicants herein, it has been found that the combination of cysteamine and a thioglycolic acid or its salt is very efficient at low pH so long as the pH is lowered without the addition of a carboxylic acid, such as citric acid. As explained, the addition of citric acid, or other carboxylic acid, has the effect of complexing at least a portion of the cationic compound, e.g., cysteamine, with the pH adjusting carboxylic acid and, thereby, significantly decreasing the wave efficiency of the waving lotion.

Figure 17:
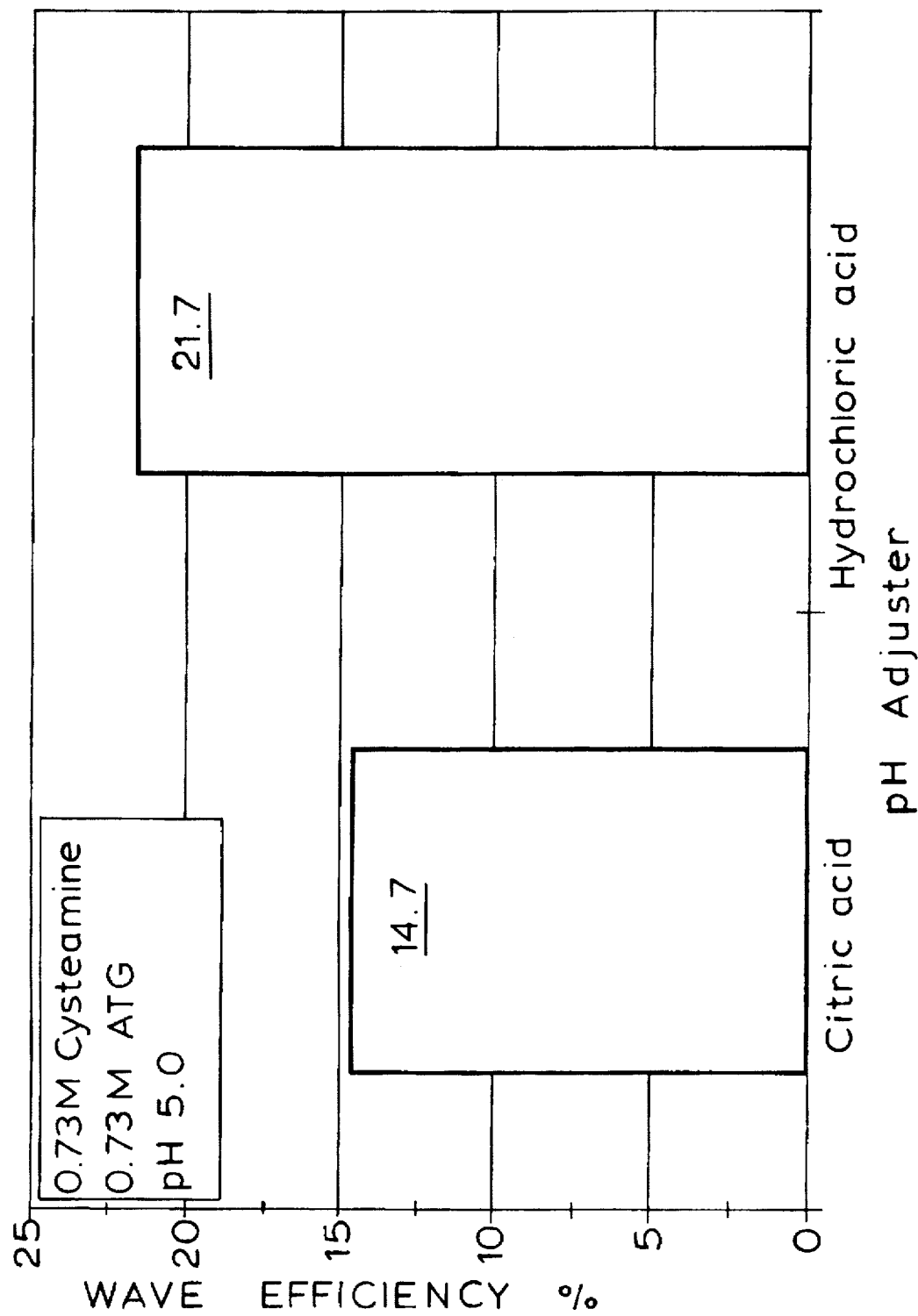
FIG. 17 is a bar graph showing the wave efficiencies of solutions of cysteamine and thioglycolic acid wherein the pH is reduced to 5.0 by the addition of a non-carboxylic acid (HCl), in accordance with the present invention, compared to the wave efficiency of the same composition reduced to pH of 5.0 with a carboxylic acid (citric)

To further substantiate the above theory, two aqueous solutions of cysteamine hydrochloride and thioglycolic acid, each at a concentration of 0.73M were prepared to a pH of 7.1, and each was titrated with an acid, one with a carboxylic acid (citric acid) and the other with a non-carboxylic acid (hydrochloric acid) to a pH of 5.0. As shown in FIG. 17, the solution titrated with citric acid had an insufficient wave efficiency of 14.7% while the solution titrated with hydrochloric acid maintained an effective wave efficiency of 21.7%.

The composition optionally can be thickened, for example, with sodium alginate, gum arabic, cellulose derivatives such as methylcellulose, hydroxyethylcellulose, hydroxypropylmethylcellulose and carboxymethylcellulose, and various polymeric thickeners, such as acrylic acid derivatives. It is also possible to use inorganic thickeners, such as bentonite. These thickeners, when included, preferably are present in an amount from about 0.1% to about 10% by weight and, in particular, from about 0.5% to about 3% by weight, based on the total weight of the composition.

The composition has the pH in the range of about 2.0 to about 12.0. To achieve the full advantage of the present invention, the composition has a pH of about 5.0 to about 10.0, particularly about 5.5 to about 8.5, especially about 7.0 for best curl retention when cold waved. This pH can be achieved by the addition of an alkanolamine, ammonia, an ammonium carbonate, or a metal hydroxide to the composition of the present invention.

Moisturizers may enhance the curl formation of the permanent wave composition of the present invention. The use of polyhydric alcohols or polyhydroxy alkane compounds, such as ethylene glycol, glycerine, propylene glycol, or polyoxyethylene glyceryl ether in this composition leave the hair in better condition due to humectant properties and surprisingly does not compromise curl formation, but provides the hair with a more uniform and natural curl.

These moisturizers are selected from the group consisting of polyhydroxyalkyl compounds, particularly alkylene glycols and polyalkylene glycols, and especially ethylene glycol and the polyethylene glycols; propylene glycol and the polypropylene glycols; polyethylene glycol glyceryl ethers; ethoxylated fatty alcohols; and fatty alcohol polyglycol ethers. Examples of suitable moisturizers include glycols and triols such as glycerine, ethylene glycol, propylene glycol, 1,3-butylene glycol, 1,2,6-hexanetriol, 1,5-pentanediol, 2-methyl pentanediol-2,4, and 2-ethyl hexanediol-1,3. Further examples of suitable moisturizers include the polyalkylene glycols, such as those compounds having the formula

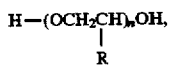

wherein R is H or $CH_3$, and n has an average value of 2 to 600; when R=H, particularly suitable moisturizers have n in the range of 4 to 600; and when R=$CH_3$, particularly suitable moisturizers have n in the range of 2 to 34. The polyalkylene glycols that can be used as moisturizers in the permanent wave composition of the present invention are exemplified by, but not limited to, compounds such as polyethylene glycol 200; polyethylene glycol 400; polyethylene glycol 600; polypropylene glycol 150; tetraethylene glycol; and dipropylene glycol.

Examples of other suitable moisturizers include the polyethylene glycol glyceryl ethers, such as polyethylene glycol 600 glyceryl ether and polyethylene glycol 26 glyceryl ether. Furthermore, the ethoxylated nonyl phenols and ethoxylated octyl phenols, particularly nonoxynol, $C_9H_{19}C_6H_4(OCH_2CH_2)_n$—OH, wherein n averages at least 6 and up to about 100; and octoxynol, $C_8H_{17}S_6H_4(OCH_2CH_2)_n$—OH, wherein n averages at least 7 and up to about 40, also are suitable moisturizers for use in the composition of the present invention. Suitable ethoxylated fatty alcohols for use as moisturizers in the composition of the present invention include compounds having the formula R—(OCH$_2$CH$_2$)$_n$OH, wherein R is an alkyl group containing from about 12 to about 30 carbon atoms and n averages at least 6. In addition, fatty alcohol polyglycol ethers having the formula

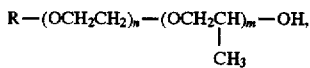

wherein R is an alkyl group containing from about 8 to about 18 carbon atoms, n=0 to 6, m=0 to 6, and n+m is at least 6, also are useful as moisturizers in the composition of the present invention.

The composition of the present invention is easy to use and apply, repeatedly, without damaging the hair while providing a strong, tight curl and leaving the hair unexpectedly soft. The composition can be lotion or water wrapped and can be used with or without heat. Unexpectedly, the composition is applied to any type of hair, regardless of structural damage to the hair, resulting in consistent curl tightness and softness.

What is claimed is:

1. A composition capable of breaking sulfur to sulfur bonds in human hair when in contact with said human hair so that said hair can be reconfigured, comprising an aqueous solution containing an ionic complex formed from a cationic compound, in solution, and an anionic compound, in solution, at a molar ratio of cationic compound to anionic compound in the range of 1:1.2 to 1.2:1, said compounds being different, wherein the cation is in solution in a concentration of about 0.2 molar to about 4.0 molar and the anion is in solution in a concentration of about 0.2 molar about 4.0 molar, said aqueous solution having a pH of about 4.5 to about 8.5 and having no acid that inter- feres with ionic complexing of said cationic and anionic compounds at the pH of the composition, thereby reducing the waving efficiency;

wherein the cationic compound, in solution, forms a cation having a formula HS—CH$_2$CH$_2$—NR$_1$R$_2$R$_3$, wherein R$_1$, R$_2$ and R$_3$, which are the same or different, are H or an alkyl group having 1 to 5 carbon atoms; and wherein the anionic compound, in solution, forms a thioglycolate anion or an anion of N-acetylcysteine.

2. The composition of claim 1, wherein the composition has a pH in the range of about 5.5 to about 8.5.

3. The composition of claim 2, wherein the composition has a pH in the range of about 6.0 to about 8.0.

4. The composition of claim 3, wherein the composition has a pH of about 7.0.

5. The composition of claim 1, wherein the cation is thiocholine.

6. The composition of claim 1, wherein the anion is

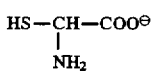

7. The composition of claim 1, wherein the anion is N-acetylcysteine.

8. The composition of claim 1, wherein the molar ratio of cationic compound to anionic compound is in the range of about 1:1.1 to about 1.1:1.

9. The composition of claim 1 wherein the cation is selected from the group consisting of cysteamine, methylcysteamine, dimethylcysteamine, trimethylcysteamine, and mixtures thereof.

10. The composition of claim 9, wherein the anion is thioglycolic acid or a salt thereof and the pH of the composition is in the range of about 5 to about 8.5.

11. The composition of claim 10, wherein the anion is monoethanolamine thioglycolate.

12. The composition of claim 1, wherein the cationic compound is thiocholine, and the anionic compound is N-acetylcysteine.

13. The composition of claim 1, wherein the cationic compound and the anionic compound are each included in the composition in a concentration of about 0.5 molar to about 2.0 molar.

14. The composition of claim 13, wherein the cationic compound and the anionic compound are each included in a concentration of about 0.5 molar to about 1.5 molar.

15. The composition of claim 14, wherein the cationic compound and the anionic compound are each included in the composition in a concentration of about 0.6 molar to about 1.0 molar.

16. The composition of claim 15, wherein the cationic compound and the anionic compound are each included in the composition in a concentration of about 0.7 molar to about 0.8 molar.

17. The composition of claim 16, wherein the cationic compound and the anionic compound are each included in the composition in a concentration of about 0.7 molar to about 0.75 molar.

18. The composition of claim 17, wherein the cationic compound and the anionic compound are each included in the composition in a concentration of about 0.73 molar.

19. A method of manufacturing a permanent wave lotion capable of forming an ionic complex between thiocholine and acetylcysteine to achieve efficient reconfiguring of human hair, said permanent wave lotion having a pH of about 4.5 to about 8.5 and having no acid that interferes with ionic complexing between said thiocholine and acetylcysteine compounds at the pH of the permanent wave lotion, thereby reducing the waving efficiency, comprising:

mixing acetylthiocholine and cysteine in water wherein the acetylthiocholine is included in a concentration in the range of about 0.2 molar to about 3.0 molar;

reacting the cysteine with the acetylthiocholine to form thiocholine and N-acetylcysteine, each in a concentration of about 0.2 molar to about 3.0 molar and in a molar ratio of thiocholine to N-acetylcysteine of 1:1.2 to 1.2:1.

20. The method of claim 19, wherein the ratio of cationic compound to anionic compound is in the range of about 1:1.1 to about 1.1:1.

21. A method of breaking sulfur to sulfur bonds in human hair so that the hair can be reconfigured, comprising:

contacting the hair with an aqueous solution containing an ionic complex formed from a cationic compound, in solution, and an anionic compound, in solution, in a molar ratio of cationic compound to anionic compound in the range of 1:1.2 to 1.2:1, said compounds being different, wherein the cation is in solution in a concentration of about 0.2 molar to about 4.0 molar and the anion is in solution in a concentration of about 0.2 molar to about 4.0 molar, said aqueous solution having a pH of about 4.5 to about 8.5 and having no acid that interferes with ionic complexing between said cationic and anionic compounds at the pH of the aqueous solution, thereby reducing the waving efficiency;

wherein the cationic compound, in solution, forms a cation having a formula HS—CH$_2$CH$_2$—NR$_1$R$_2$R$_3$, wherein R$_1$, R$_2$, and R$_3$, which are the same or different, are H or an alkyl group having 1 to 5 carbon atoms; and wherein the anionic compound, in solution, forms a thioglycolate anion or an anion of N-acetyl cysteamine.

22. The method of claim 21, wherein the ratio of cationic compound to anionic compound is in the range of about 1:1.1 to about 1.1:1.

23. A composition capable of breaking sulfur to sulfur bonds in human hair when in contact with the human hair so that the hair can be reconfigured, said composition comprising an aqueous solution containing an ionic complex formed a cationic compound, in solution, and an anionic compound, in solution, at a molar ratio of cationic compound to anionic compound of 1:1.2 to 1.2:1, wherein the cation is in solution in a concentration of about 0.2 molar to about 4.0 molar and the anion is in solution in a concentration of about 0.2 molar to about 4.0 molar, said composition having a pH of about 4.5 to about 8.5 and having no acid that interferes with ionic complexing of the cationic and anionic compounds at the pH of the composition thereby reducing waving efficiency, wherein the cationic compound, in solution, forms a cation having a formula:

$$HS-CH_2CH_2-NR_1R_2R_3^+,$$

wherein $R_1$, $R_2$, and $R_3$, which are the same or different, are H or a methyl group; and wherein the anionic compound, in solution, forms a thioglycolate anion or an anion of N-acetylcysteine.

24. The composition of claim 1 wherein the anion is thioglycolic acid or a salt thereof.

25. The composition of claim 24 wherein the anion is monoethanolamine thioglycolate.

26. The composition of claim 1 wherein the anion is N-acetylcysteine or a salt thereof.

27. The composition of claim 1 wherein the cation has the formula $HS-CH_2CH_2-NH_3^+$.

28. The composition of claim 1 wherein the cation has the formula $$HS-CH_2CH_2-\underset{\underset{CH_3}{|}}{NH_2^+}.$$

29. The composition of claim 1 wherein the cation has the formula $$HS-CH_2CH_2-\underset{\underset{CH_3}{|}}{\overset{\overset{CH_3}{|}}{N}H^+}.$$

30. The composition of claim 1 wherein the cation has the formula $$HS-CH_2CH_2-\underset{\underset{CH_3}{|}}{\overset{\overset{CH_3}{|}}{N^+}}-CH_3.$$

31. The composition of claim 1 wherein the anionic compound is monoethanolamine thioglycolate or N-acetylcysteine, and cationic compound is cysteamine.

32. The composition of claim 1 wherein the anionic compound is monoethanolamine thioglycolate, and the cationic compound is dimethylcysteamine.

* * * * *